US007979214B2

(12) United States Patent
Jarman et al.

(10) Patent No.: US 7,979,214 B2
(45) Date of Patent: Jul. 12, 2011

(54) PEPTIDE IDENTIFICATION

(75) Inventors: Kristin H. Jarman, Richland, WA (US); William R. Cannon, Richland, WA (US); Kenneth D. Jarman, Richland, WA (US); Alejandro Heredia-Langner, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1215 days.

(21) Appl. No.: 11/592,610

(22) Filed: Nov. 3, 2006

(65) Prior Publication Data

US 2007/0055458 A1 Mar. 8, 2007

Related U.S. Application Data

(62) Division of application No. 10/361,275, filed on Feb. 10, 2003, now abandoned.

(51) Int. Cl.
*G01N 33/50* (2006.01)

(52) U.S. Cl. ............... 702/19; 436/173; 702/27; 702/30

(58) Field of Classification Search ........................ None
See application file for complete search history.

(56) References Cited

U.S. PATENT DOCUMENTS 6,487,523 B2 11/2002 Jarman et al.

FOREIGN PATENT DOCUMENTS

WO WO 99/62930 12/1999
WO WO 2004/008371 1/2004

OTHER PUBLICATIONS

Pevzner et al. (Genome Res. 2001 11: 290-299).*

Pevzner et al. (Journal of Computational Biology, vol. 7, No. 6, pp. 777-787, Mary Ann Liebert, Inc., 2000).*

Dasgupta et al. (In the proceedings of the Genetic and Evolutionary Computation (GECCO) Conference, Jul. 13-17, 1999, Orlando, pp. 149-155).*

Bafna et al., "SCOPE: A probabilistic model for scoring tandem mass spectra against a peptide database," *Bioinformatics*, vol. 17, Suppl. 1, pp. S13-S21 (2001).

Clauser et al., "Role of Accurate Mass Measurement (10 ppm) in Protein Identification Strategies Employing MS or MS/MS and Database Searching," *Analytical Chemistry*, vol. 71, pp. 2871-2882 (1999).

Dančík et al., "*De Novo* Peptide Sequencing via Tandem Mass Spectrometry," *Journal of Computational Biology*, vol. 6, No. 3/4, pp. 327-342 (1999).

Eng et al., "An Approach to Correlate Tandem Mass Spectral Data of Peptides with Amino Acid Sequences in a Protein Database," *Journal of American Society of Mass Spectrometry*, vol. 5, pp. 976-989 (1994).

Gras et al., "Improving protein identification from peptide mass fingerprinting through a parameterized multi-level scoring algorithm and an optimized peak detection," *Electrophoresis*, vol. 20, pp. 3535-3550 (1999).

Heredia-Langner et al., "De Novo Analysis of Tandem Mass Spectrometry Data as a Non-Deterministic Optimization Problem," *Proc. International MultiConference in Computer Science and Computer Engineering*, 5 pp. (2004).

Heredia-Langner et al., "Sequence optimization as an alternative to de novo analysis of tandem mass spectrometry data," *Bioinformatics*, vol. 20, No. 14, pp. 2296-2304 (2004).

Jarman et al., "A New Statistically-Based Scoring Method for Peptide Identification via Tandem Mass Spectrometry," *Analytical Chemistry*, 25 pp. (document marked as being submitted Dec. 2002).

Jarman et al., "An Algorithm for Automated Bacterial Identification Using Matrix-Assisted Laser Desorption/Ionization Mass Spectrometry," *Analytical Chemistry*, vol. 72, pp. 1217-1223 (Mar. 2000).

Jarman et al., "Extracting and Visualizing Matrix-assisted Laser Desorption/Ionization Time-of-flight Mass Spectral Fingerprints," *Rapid Communications in Mass Spectrometry*, vol. 13, pp. 1586-1594 (1999).

Malard et al., "Constrained De Novo Peptide Identification via Multi-objective Optimization," *Proc. IEEE International Workshop on High Performance Computational Biology*, 8 pp. (2004).

Parker, "Scoring methods in MALDI peptide mass fingerprinting: Chemscore and the ChemApplex program," *Journal of American Society of Mass Spectrometry*, vol. 13, pp. 22-39 (2002).

Perkins et al., "Probability-based protein identification by searching sequence databases using mass spectrometry data," *Electrophoresis*, vol. 20, pp. 3551-3567 (1999).

Petritis et al., "Use of Artificial Neural Networks for the Accurate Prediction of Peptide Liquid Chromatography Elution Times in Proteome Analyses," *Analytical Chemistry*, vol. 75, No. 5, pp. 1039-1048 (Mar. 2003).

Stranz et al., "Derivation of Peptide Sequence from Mass Spectral Data using the Genetic Algorithm," downloaded from http://www.abrf.org/JBT/Articles/JBT0004/JBT0004.html, 9 pp. (document marked 1998).

Wahl et al., "Analysis of Microbial Mixtures by Matrix-Assisted Laser Desorption/Ionization Time-of-Flight Mass Spectrometry," *Analytical Chemistry*, vol. 74, No. 24, pp. 6191-6199 (Dec. 15, 2002).

Zhang et al., "ProFound: An Expert System for Protein Identification Using Mass Spectrometric Peptide Mapping Information," *Analytical Chemistry*, vol. 72, No. 11, pp. 2482-2489 (Jun. 1, 2000).

* cited by examiner

*Primary Examiner* — Karlheinz R Skowronek
(74) *Attorney, Agent, or Firm* — Klarquist Sparkman, LLP

(57) ABSTRACT

Peptides are identified from a list of candidates using collision-induced dissociation tandem mass spectrometry data. A probabilistic model for the occurrence of spectral peaks corresponding to frequently observed partial peptide fragment ions is applied. As part of the identification procedure, a probability score is produced that indicates the likelihood of any given candidate being the correct match. The statistical significance of the score is known without necessarily having reference to the actual identity of the peptide. In one form of the invention, a genetic algorithm is applied to candidate peptides using an objective function that takes into account the number of shifted peaks appearing in the candidate spectrum relative to the test spectrum.

18 Claims, 11 Drawing Sheets

PEPTIDE IDENTIFICATION

CROSS REFERENCE TO RELATED APPLICATION

This is a division of application Ser. No. 10/361,275, filed Feb. 10, 2003 (now abandoned), which is incorporated herein by reference.

ACKNOWLEDGMENT OF GOVERNMENT SUPPORT

This invention was made with Government support under Contract DE-AC06-76RL01830, awarded by the U.S. Department of Energy. The United States Government may have certain rights in the invention.

REFERENCE TO SEQUENCE LISTING

The sequence listing submitted in connection with this disclosure, the listing amounting to twelve pages in paper form and a corresponding computer-readable form, in incorporated herein by reference.

BACKGROUND

The present invention relates to identification of peptides based on their mass spectrometry (MS) characteristics.

High-throughput proteomic technologies seek to characterize the state of the proteome in a cell population in much the same manner that DNA microarrays seek to characterize the state of gene expression in a cell population. Characterization of the proteins can be done using several different methods, one of which is to digest the proteins first, typically using trypsin, into peptides which are then analyzed using tandem mass spectrometry (MS/MS). A typical procedure may involve extracting cellular proteins followed by tryptic digestion and then separating the peptides with liquid chromatography. The separated peptides are then identified by MS/MS. Ideally, peptides will subsequently be quantitated, post-translational modifications will be determined and the information regarding the peptides will be assembled into a picture of the proteomic state of a cell population in, into peptides which are then analyzed using tandem mass spectrometry (MS/MS). A typical procedure may involve extracting cellular proteins followed by tryptic digestion and then separating the peptides with liquid chromatography. The separated peptides are then identified by MS/MS. Ideally, peptides will subsequently be quantitated, post-translational modifications will be determined and the information regarding the peptides will be assembled into a picture of the proteomic state of a cell population.

Just as with DNA microarrays, quality assurance of the high-throughput process is of paramount importance in order for proteomics to be of value to biologists. If peptides are initially identified poorly, then this information and the information on post-translational state and quantitation of protein expression is not of much value. For this reason, there has been much work recently on developing peptide identification methods for MS/MS spectra. This area of research has proceeded on two fronts, the first of which seeks to take advantage of the wide availability of genome sequences. The database search methods try to identify the peptide that resulted in the observed MS/MS spectrum by picking the best candidate from a list of peptides generated from the genome sequence (e.g. Eng, K.; McCormack, A. L.; Yates, J. R. I. *J Am Soc of Mass Spec* 1994, 5, 976-989). De novo methods on the other hand, seek to sequence and hence identify a peptide simply from the observed MS/MS spectrum (e.g. Dančik, V.; Addona, T. A.; Clauser, K. R.; Vath, J. E.; Pevzner, P. A. *J. Comput. Biol.* 1999, 6, 327-342 ("Dančik et al." herein). Regardless of which approach is used, it is essential to have a method for scoring each peptide so that accurate and reliable identifications can be made.

SEQUEST, for example, scores peptides by calculating the overlap integral between a model spectrum for a peptide and the experimental spectrum. Both the model spectrum and the experimental spectrum are transformed into continuous functions in order to calculate the overlap integral. This approach has been successful as measured by the number of labs that use it. However, interpretation of the scores is not straightforward, and statistical confidence in the identification of the highest-scoring peptide remains in question. Criteria based on experience and on a more rigorous statistical analysis have been proposed to construct scoring thresholds above which an identification should be accepted.

Dančik et al. developed a more rigorous scoring scheme for use with de novo sequencing of peptides. De novo sequencing methods have not been as widely used as methods that identify the best peptides from a candidate list for several reasons. First, MS/MS spectra often do not contain enough information to allow for unambiguous determination of the entire peptide sequence. It has been estimated that 50% of spectra are missing enough peaks to allow only partial interpretation. Second, de novo approaches can be computationally intensive, which is an important criterion for high-throughput proteomics. Still, there is a significant need for de novo sequencing methods because often the most biologically interesting peptides, such as those containing mutations and frameshifts, may not be in the sequence database to begin with. This will be especially true in clinical or field settings where the genome of the organism being studied differs from the genome of the organism that was sequenced.

An ideal MS/MS spectral analysis would have several desirable features. The scoring method would ideally report, as the score, the probability of a spectrum being due to a particular peptide. Short of that, the scoring would contain a rigorous test of significance of the results. Also, the scoring method should be well characterized as far as its rate of producing both false positive and false negative identifications. In addition, a combined analysis in which partial peptide sequences determined de novo can be scored alongside peptides obtained from a sequence-specific peptide database in a statistically meaningful manner is desirable. Such an ideal computational analysis would have the speed seen with database peptide identification programs, the unbiased nature of a de novo method, and statistically rigorous scoring.

SUMMARY

It is an object of the present invention to provide an improved method for identifying unknown peptides from a MS/MS spectrum. Another object is to provide such a method that is computationally efficient in database and de novo analysis, conducive to high-throughput processing.

These objects and others are achieved by various forms of the present invention. One form of the present invention comprises a statistically rigorous scoring algorithm for peptide identification that can be used alone, or incorporated into a database search algorithm or a de novo peptide sequencing algorithm. This form is based on a probabilistic model for the occurrence of spectral peaks corresponding to key partial peptide ion types. In particular, the ion frequencies for the most frequently observed ion types are initially estimated from a training data set of known sequences. These frequencies are then used to construct a fingerprint for any candidate peptide of interest, where the fingerprint consists of a list of spectral peaks and their corresponding probabilities of appearance. A spectrum is then scored against the candidate fingerprints using a likelihood ratio between the hypothesis that the candidate peptide is not present and the hypothesis that the candidate peptide is present. This likelihood ratio can be used for peptide identification. In addition, a probabilistic score that estimates the probability of a candidate peptide being present in the test sample can be constructed from the likelihood ratio. This approach is applied to a large data set of over 2000 spectra for tryptic peptides of different lengths ranging from 6-mer to 30-mer amino acids, all having a precursor ion charge of +2. Performance results indicate that this approach is accurate, and consistent across different peptide lengths and experimental conditions. False positive and false negative error rates for sequence length 10-mer and shorter are generally below 5%, while error rates for sequences longer than 10-mer are typically below 3%.

In one disclosed form of the invention, a Genetic Algorithm is applied to find peptide sequences that are relatively close matches to a sample. Techniques are applied to select a new generation of candidates from an old generation, and an objective function is provided that takes into account peaks that appear to be shifted in one spectrum relative to another.

DESCRIPTION

Figure 1:
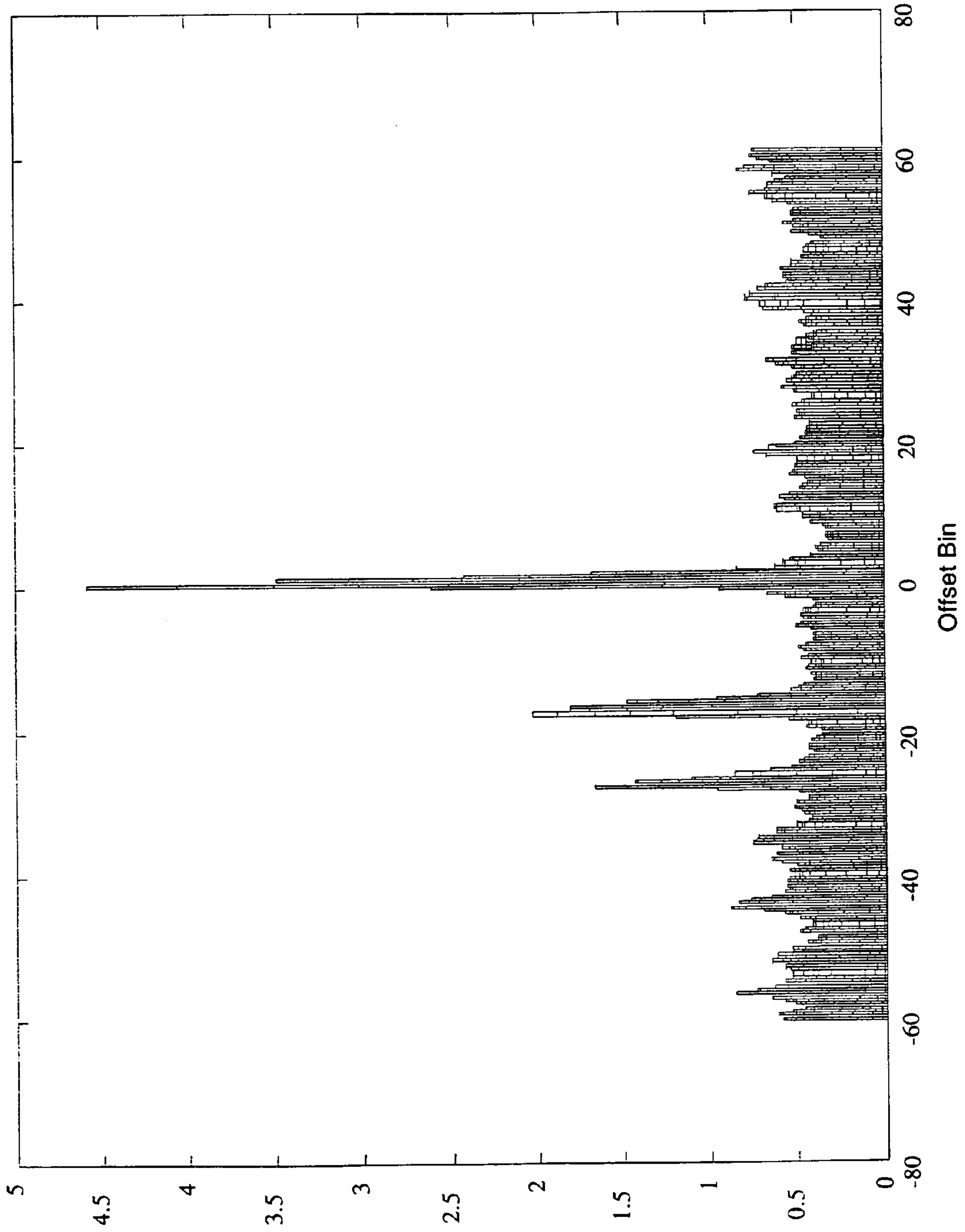
FIG. 1 is a histogram of ion frequencies versus offset bin for N-terminus partial peptide sequences generated from 10-mers in an experimental application of the present invention. Individual histograms for ion offsets for each partial peptide from length 1 to 9 are colored and stacked to present a summary view of the ion offset patterns that are found.

For the purpose of promoting an understanding of the principles of the present invention, reference will now be made to the embodiment illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein are contemplated as would normally occur to one skilled in the art to which the invention relates.

Generally, the method whose results are illustrated in FIGS. 1-6 provides an improved method for identifying peptides based on a MS/MS spectral analysis.

EXPERIMENTAL METHODS

Description of Spectra

Peptides were derived from *Deinococcus radiodurans* by tryptic digestion and mass analyzed. Briefly, the 2719 CID spectra for the 1297 peptides analyzed in the present embodiment were obtained using an electrospray ionization source feeding a Finnigan LCQ Classic ion trap. The spectra were all output in centroid mode. Initial independent identifications were done with SEQUEST using an organism-specific sequence database and using a multi-run MS/MS strategy. Each peptide was analyzed multiple times on multiple days with the LCQ and at least one spectrum for each peptide resulted in SEQUEST Xcorr scores exceeding 2. Next, the mass of each peptide parent ion was confirmed to within one part-per-million of the theoretical mass for that peptide by the use of an 11.5 Tesla ion-cyclotron resonance mass spectrometer and a 15% elution time tolerance.

Numerical Methods

The methods discussed herein for scoring candidate peptide sequences builds on the method of Jarman, K. H.; Daly, D. S.; Petersen, C. E.; Saenz, A. J.; Valentine, N. B.; Wahl, K. L. *Rapid Commun Mass Spectrom* 1999, 13, 1586-1594; Jarman, K. H.; Cebula, S. T.; Saenz, A. J.; Petersen, C. E.; Valentine, N. B.; Kingsley, M. T.; Wahl, K. L. *Anal Chem* 2000, 72, 1217-1223; Wahl, K.; Wunschel, S.; Jarman, K.; Valentine, N.; Petersen, C.; Kingsley, M.; Zartolas, K.; Saenz, A. *Anal Chem* 2002, 74, 6191-6199, for bacterial identification using matrix-assisted laser desorption ionization (MALDI) time-of-flight mass spectrometry. For each candidate sequence, a fingerprint spectrum is constructed consisting of a list of key biomarkers along with an estimate of the frequency of occurrence for each biomarker. In a test spectrum, any fingerprint biomarkers appearing are extracted and compared to the fingerprint. A score is computed that is a likelihood ratio between the hypothesis that the test spectrum is due to the candidate sequence versus the hypothesis that the test spectrum is simply due to chance. The remainder of this section describes the fingerprint construction and scoring algorithms.

Fingerprint Construction

The MS/MS fingerprint for a candidate sequence is defined to be the location, uncertainty in location, and the frequency of appearance for key peaks. More specifically, for a peptide of length P, a fingerprint is defined by $F=\{l_{r,i}, s_{r,i}, p_{r,i}\}$ for respective C- and N-terminus ions $r=C_1, C_2, \ldots C_P, N_1, N_2, \ldots N_P$, and ion types $i=1, 2, \ldots I$, where $C_1$ indicates the C-terminus fragment with a single amino acid residue, similarly for $N_1$, and so on. For each peak, defined by the pair (r, i), the parameter $l_{r,i}$ is the peak location, $s_{r,i}$ is the variability in location, and $p_{r,i}$ is the fraction of replicate spectra in which the peak is expected to be observed. Clearly, the peak locations and their corresponding variability are key parameters for comparing a test spectrum to a fingerprint. However, we note that the parameter $p_{r,i}$ is also important here in that it takes into account the reality that missing or low concentration fragments and errors in peak detection lead to occasional missing peaks.

Variability in peak location $s_{r,i}$ is specified by the instrument tolerance in this implementation. Fingerprint peak locations and frequencies of appearance are computed using a method for learned ion types derived from work by Dančik et al. Locations for a candidate fingerprint are constructed from the sum of residue masses of the amino acids composing the partial peptide molecular weights, offset by an amount determined by the most frequent ion types learned a priori from a set of training spectra. In particular, for a given C-terminus (N-terminus) partial sequence, a peak is potentially produced at location $l_{r,i}=m_r+d_{r,i}$ with some probability $p_{r,i}$ where $m_r$ is the sum of residue masses in the partial peptide, and $d_{r,i}$ is an offset determined by the ion types produced during fragmentation. For example, $d_{r,i}\approx 19$ for a C-terminus y ion, where we use approximately equal to because of instrument variability in peak location.

The fingerprint offsets $d_{r,i}$ are computed from a set of training spectra as follows. For each C-terminus (N-terminus) fragment r, we count the frequency of appearance or fraction of spectra in which peaks of varying binned offsets appear. For inclusion into the fingerprint, we sum the frequencies over all C-terminus (N-terminus) fragments and choose the two offsets corresponding to the two most frequent, nonadjacent offset bins. We use two offsets for each fragment type in hopes of capturing the most prominent ion types for each fragment. (For example, y and either y-$H_2O$ or y-$NH_3$ are generally the most prominent ion types for C-terminal fragments.)

The fingerprint probabilities $p_{r,i}$ are taken to be the frequency of appearance for each C-terminus (N-terminus) fragment r corresponding to the two most prominent offsets. We note that the frequencies of appearance for each offset bin include peaks appearing by chance in addition to peaks associated with a given ion. Therefore, the fingerprint probabilities tend to be overly optimistic. If the occurrence of peaks in a particular offset bin purely by chance is low, this false increase of frequencies will not be a serious problem. In the present embodiment, we have tried to limit the effects of peaks falling in offset bins by chance by filtering small, insignificant peaks from the spectra prior to computing frequencies of appearance and scoring as described below. Other methods for overcoming this limitation are also within the scope of the present invention.

Scoring Algorithm

The scoring procedure in this example embodiment computes a likelihood ratio between the null hypothesis that a given candidate sequence is not in the sample versus the alternate hypothesis that the candidate sequence is the source of the test spectrum.

$H_0$: a random sequence (not the candidate) is present $H_A$: the candidate sequence is present For a candidate sequence, the scoring procedure employs three steps. In the first step, a peak table is constructed from the test spectrum that contains the list of the peak locations of any significant peaks. In the second step, fingerprint peaks appearing in the peak table of the test spectrum are extracted using a prediction interval based on the tolerance parameter $s_{r,i}$ for each peak.

The likelihood ratio is computed in the third step of the process. Under the alternate hypothesis, $H_A$, the frequency of appearance of a peak at fingerprint peak location, $l_{r,i}$ is given by the probability $p_{r,i}$ estimated from the reference fingerprint. Under the null hypothesis, $H_0$, the frequency of appearance of a peak at location, $l_{r,i}$ is given by $q_{r,i}$ estimated to be the probability of a peak appearing at that location purely by chance when some random peptide is present.

The probabilities $q_{r,i}$ are computed as follows. Under $H_0$, we assume that the test spectrum results from an unknown sequence. In this case, a peak may occur at location $l_{r,i}$ because (a) the partial sequence r is contained in the unknown sequence and results in a peak, or (b) purely by chance. Assuming that all amino acid combinations are equally likely, the probability of observing a peak at $l_{r,i}$ due to (a) is approximated by $$\pi_{r,i} = \left(\frac{1}{|A|}\right)^{N_R} p_{r,i} \tag{1}$$

where |A| is the number of amino acids, $N_R$ is the partial peptide length, and $p_{r,i}$ is the frequency of appearance for that partial sequence under the alternate hypothesis. The probability of observing $l_{r,i}$ due to chance alone is $$\omega_{r,i} = \left\{1 - \left(\frac{1}{|A|}\right)^{N_R}\right\} q_0 \tag{2}$$

where $$q_0 = N_{pks}\frac{tol}{\max(mz) - \min(mz)} \tag{3}$$

for a test spectrum containing $N_{pks}$ peaks, with m/z tolerance tol and mass range max(mz)-min(mz). We note that $q_0$ approximates the probability of a random peak appearing at any specific location assuming peaks are uniformly distributed about the mass range of interest. The probability $q_{r,i}$ is then given by $$q_{r,i}=\pi_{r,i}+\omega_{r,i} \tag{4}$$

Let the vector $\underline{x}$ represent appearance of fingerprint peaks in the test spectrum where $x_{r,i}=0$ if fingerprint peak (r, i) is not observed in the test spectrum, and $x_{r,i}=1$ if fingerprint peak (r, i) is observed in the test spectrum. Assuming that the appearance of peaks at different locations is independent, then the likelihood ratio for $H_0$ versus $H_A$ is given by the probability of observing the outcome under $H_A$ divided by the probability of observing the outcome under $H_0$. Specifically, the likelihood ratio score for a given candidate is L, where $$L = \frac{P\{\text{outcome under } H_A\}}{P\{\text{outcome under } H_0\}} = \frac{\prod_{r,i} p_{r,i}^{x_{r,i}} \prod_{r,i} (1-p_{r,i})^{1-x_{r,i}}}{\prod_{r,i} q_{r,i}^{x_{r,i}} \prod_{r,i} (1-q_{r,i})^{1-x_{r,i}}} \tag{5}$$

In determining significance for a given sequence, we take the log-likelihood ratio $$\lambda = \sum_{r,i} \log\left(\frac{1-p_{r,i}}{1-q_{r,i}}\right) + \sum_{r,i} x_{r,i} \log\left[\frac{p_{r,i}(1-q_{r,i})}{q_{r,i}(1-p_{r,i})}\right] \tag{6}$$

and apply the following decision rule:

If •≦$K_c$, then decide $H_0$,

If •>$K_c$, then decide $H_A$

Where $K_c$ is the critical decision threshold. If $H_A$ is decided, the candidate sequence is determined to be present in the unknown sample.

The critical threshold $K_c$ can be determined empirically to be the value that minimizes the combined the false and missed positive rates for a test data set. We call this threshold for peptide identification the likelihood ratio criterion.

In practice, we use only fingerprint peaks whose frequency of appearance exceeds $q_0$ (the probability of observing a peak at random) when forming the likelihood ratio. This ensures that the scoring procedure is using peaks that have a different probability of appearance under $H_0$ and $H_A$, so that the occurrence of each fingerprint peak for a given candidate is expected to be more frequent that by chance alone. We call this value the cut-off frequency for scoring.

Alternatively, the likelihood ratio (5) can be used to construct a probability that a candidate sequence is present in the sample, and this probability can be used for peptide identification. Assuming the correct sequence is one of the $N_{cand}$ candidate fingerprints, Bayes decision analysis can be used to construct the probability of $H_A$ given the test spectrum, where $$P\{H_A \mid \underline{x}\} = \frac{P\{\underline{x} \mid H_A\}P\{H_A\}}{P\{\underline{x} \mid H_A\}P\{H_A\} + P\{\underline{x} \mid H_0\}P\{H_0\}} = \frac{1}{1 + \frac{P\{\underline{x} \mid H_0\}P\{H_0\}}{P\{\underline{x} \mid H_A\}P\{H_A\}}} \tag{7}$$

-continued $$= \frac{1}{1 + \frac{\prod_{r,i} q_{r,i}^{x_{r,i}} \prod_{r,i} (1-q_{r,i})^{1-x_{r,i}} \frac{N_{cand}-1}{N_{cand}}}{\prod_{r,i} p_{r,i}^{x_{r,i}} \prod_{r,i} (1-p_{r,i})^{1-x_{r,i}} \frac{1}{N_{cand}}}} = \frac{1}{1 + \frac{1}{L}(N_{cand}-1)}$$

We note that for a given value L, (7) decreases as $N_{cand}$ increases. This is due to the fact that increasing the number of comparisons $N_{cand}$ increases the chance of erroneously observing a high likelihood L, thereby decreasing the probability that any given sequence is the correct one.

Experimental Results and Discussion

Performance of the peptide identification approach discussed above is evaluated on a test data set consisting of 2719 MS/MS spectra and 1297 candidate peptide fingerprints. These spectra were randomly selected from a larger database containing MS/MS spectra due to precursor ions with a charge of +2. Each peptide was observed multiple times and analyzed by SEQUEST. It was required that in at least one of the MS/MS runs for each peptide, the SEQUEST Xcorr score exceeded 2. Next, the mass of this peptide was verified by FTICR MS to be within 1 ppm of the theoretical mass calculated from the peptide sequence. The error rate resulting from this process is expected to be small. A large number of MS/MS spectra arising from known peptides is preferred for the improved performance evaluation of the present method and comprehensive statistical comparison with other MS/MS peptide identification methods.

The method discussed herein for peptide identification was implemented in MATLAB v6.1 (published by The MathWorks, Inc.). The data set was partitioned into MS/MS spectra for peptides of different lengths, ranging from 6-mers to 30-mers. For each partition, fingerprints were constructed from each unique sequence, and those fingerprints comprised the list of candidate sequences used in peptide identification. Table 1 provides the number of test spectra and the number of fingerprints for each partition used in this experiment.

TABLE 1

Test Data Set Summary.

| Peptide Length | # of Test Spectra | # of Fingerprints | Peptide Length | # of Test Spectra | # of Fingerprints |
|---|---|---|---|---|---|
| 6 | 259 | 169 | 20 | 260 | 123 |
| 8 | 182 | 152 | 23 | 285 | 117 |
| 10 | 273 | 150 | 26 | 257 | 81 |
| 12 | 211 | 126 | 30 | 264 | 64 |
| 14 | 220 | 130 | Total | 2719 | 1297 |
| 17 | 508 | 185 | | | |

Figure 2:
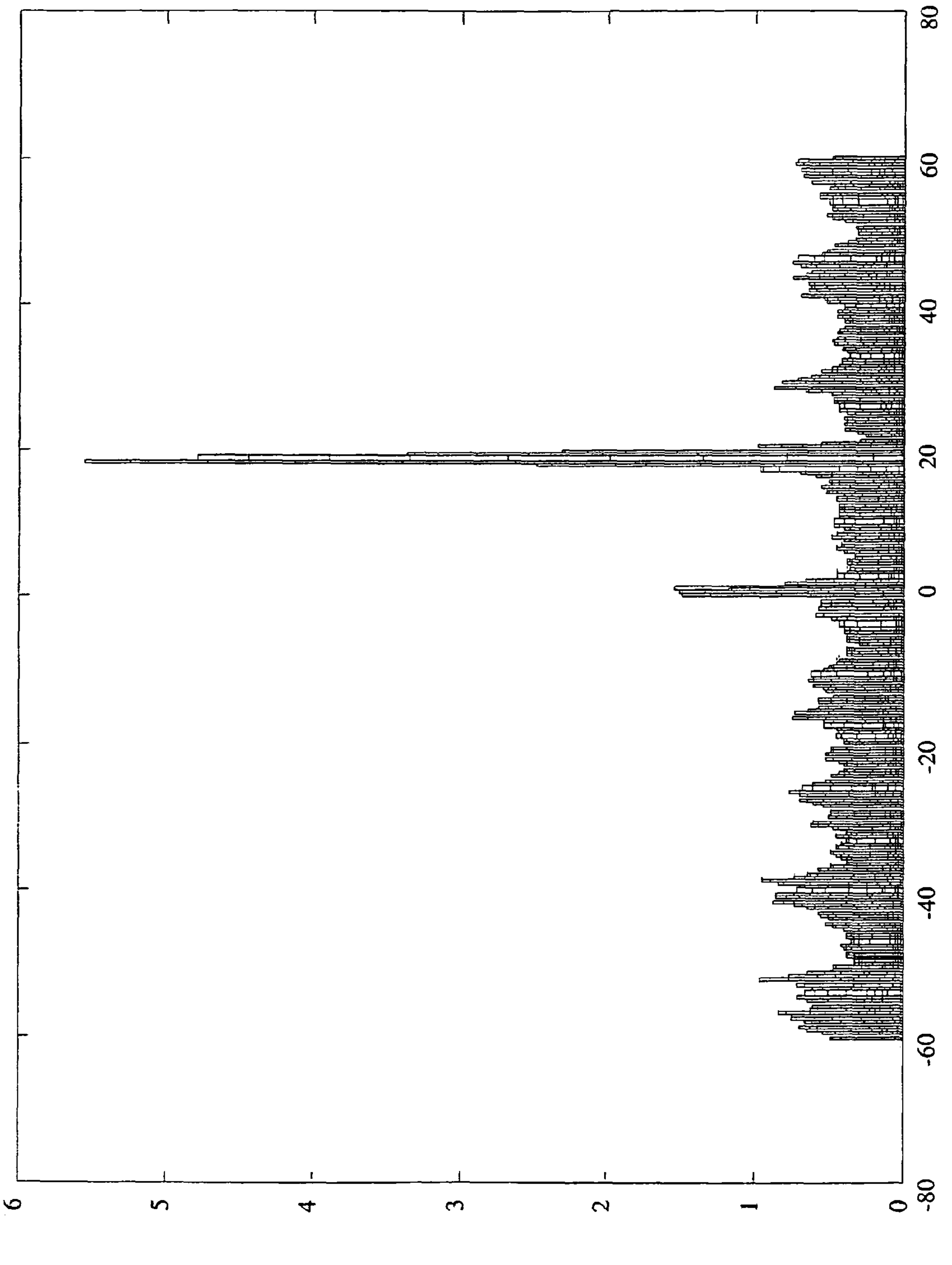
FIG. 2 is a histogram of ion frequencies versus offset bin for C-terminus partial peptide sequences generated from 10-mers in an experimental application of the present invention. Individual histograms for ion offsets for each partial peptide from length 1 to 9 are colored and stacked to present a summary view of the ion offset patterns that are found.

For each partition, the MS/MS fingerprints are constructed from the partial peptide masses and most frequent ion offsets as described in the previous section, where the bin width is set to 0.5 Da. FIGS. 1 and 2 illustrate the cumulative offset frequencies for a test set of 10-mer spectra as a function of offset. Note that the figures represent histograms of offset frequencies constructed from many spectra. Consistent with work by Dančik, et al. and with common assumptions about the frequency of appearance of the principal ion types, the most prominent offsets observed in this test set correspond to the y, y-$H_2O$, b, and b-$H_2O$ ions. Table 2 reports the fingerprint ion offsets (two most frequent ion offsets for each ion type) used in each data partition. The fingerprint offsets are very consistent across the different partitions, and are also consistent with the most frequent ion types reported by Dančik, et al. In particular, the fingerprint offsets for the C-terminus ions are consistently 18.5 and 0.5, and the fingerprint offsets for the N-terminus ions are consistently 0.5 and −17.5.

TABLE 2

Fingerprint Ion Offsets for Test Data Set

| | Singly Charged N-Terminus Ions | | Singly Charged C-Terminus Ions | |
|---|---|---|---|---|
| Peptide Length | Most Frequent Offset | $2^{nd}$ Most Frequent Offset | Most Frequent Offset | $2^{nd}$ Most Frequent Offset |
| 6 | 0.5 | −18.5 | 18.5 | 0.5 |
| 8 | 0.5 | −16.5 | 18.5 | 0.5 |
| 10 | 0.5 | −17.5 | 18.5 | 0.5 |
| 12 | 0.5 | −17.5 | 18.5 | 1.5 |
| 14 | 0.5 | −17.5 | 18.5 | 1.0 |
| 17 | 0.5 | −17.5 | 18.5 | 0.5 |
| 20 | 0 | −17.5 | 18.5 | 0.5 |
| 23 | 0.5 | −17.5 | 18.5 | 0.5 |
| 26 | 0 | −17.5 | 18.5 | 0.5 |
| 30 | 0 | −17.5 | 18.5 | 0.5 |

Figure 3:
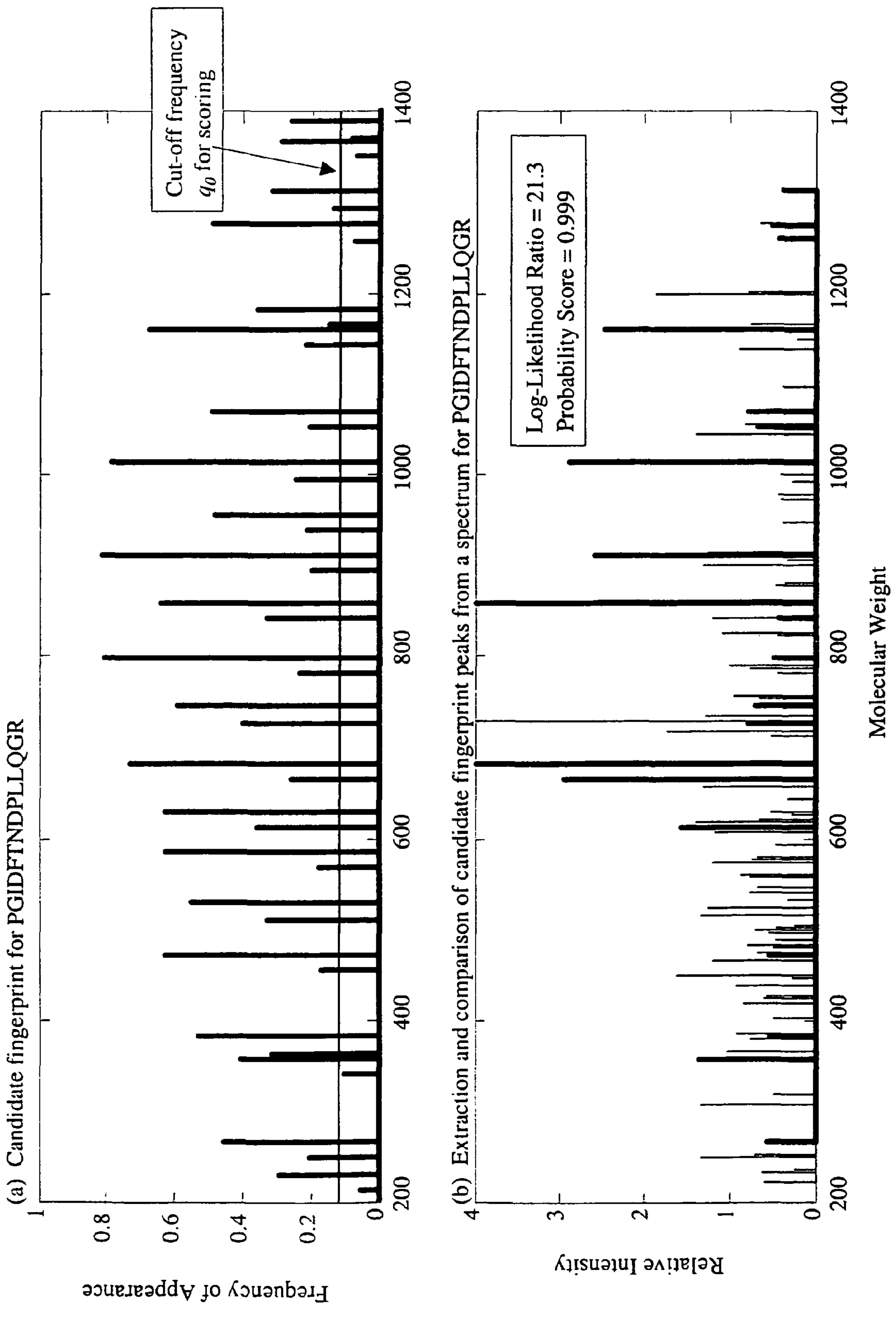
FIG. 3 is an illustration of a peptide scoring method for SEQ ID NO: 1 (PGIDFTNDPLLQGR) in an experimental application of the present invention. Subplot (a) shows the candidate fingerprint where peak location is plotted on the x-axis and frequency of appearance is plotted on the y-axis. Subplot (b) illustrates the scoring algorithm on a spectrum for SEQ ID NO: 1 (PGIDFTNDPLLQGR), where the lighter lines denote non-fingerprint peaks, and the black lines denote observed fingerprint peaks.

The peptide scoring algorithm is illustrated in FIG. 3. Subplot (a) shows the candidate fingerprint generated for the 14-mer SEQ ID NO: 1 (PGIDFINDPLLQGR). We note that the y-axis of subplot (a) represents the frequency of appearance for each spectral peak, rather than relative intensity typically plotted for MS data. Note that frequency of appearance has been substituted for relative intensity in this plot since relative intensities are not used in the scoring algorithm discussed herein. Rather, the frequency of appearance is the key parameter for scoring each peak. Note also that the frequency of appearance for each fingerprint peak is different. This is because the offset frequencies are computed separately for each partial peptide length so that the fingerprint frequencies of appearance depend on position (at which residue position along the peptide fragmentation occurs) as well as fragment ion type.

Subplot (b) in FIG. 3 illustrates the scoring method. The spectral peaks are plotted in light gray, while the fingerprint peaks for SEQ ID NO: 1 PGIDFTNDPLLQGR) extracted from the spectrum are plotted in black. We note that the horizontal line in subplot (a) shows the cutoff probability of observing a peak at any location purely by chance. Therefore, only fingerprint peaks exceeding this threshold are included in the scoring procedure. In this case, the likelihood ratio (log-likelihood ratio) is $1.72\times10^9$ (21.3), and the probability score is 0.999, resulting in a correct positive match between the test spectrum and the candidate fingerprint.

Figure 4:
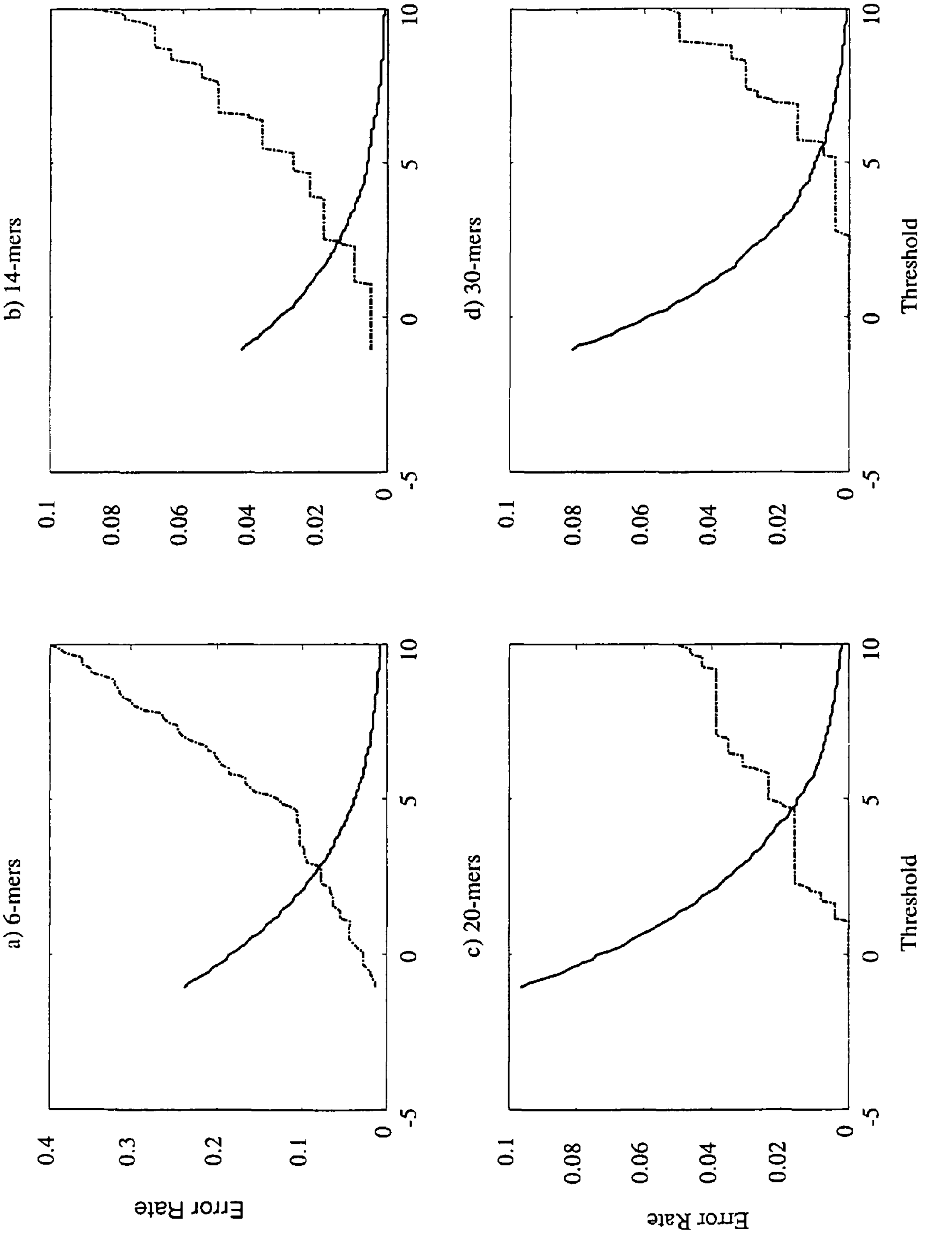
FIG. 4 is a graph of the false positive (solid line) and false negative (dashed line) rates versus critical threshold for peptide identification using likelihood ratio criteria in an experimental application of the present invention.
Figure 5:
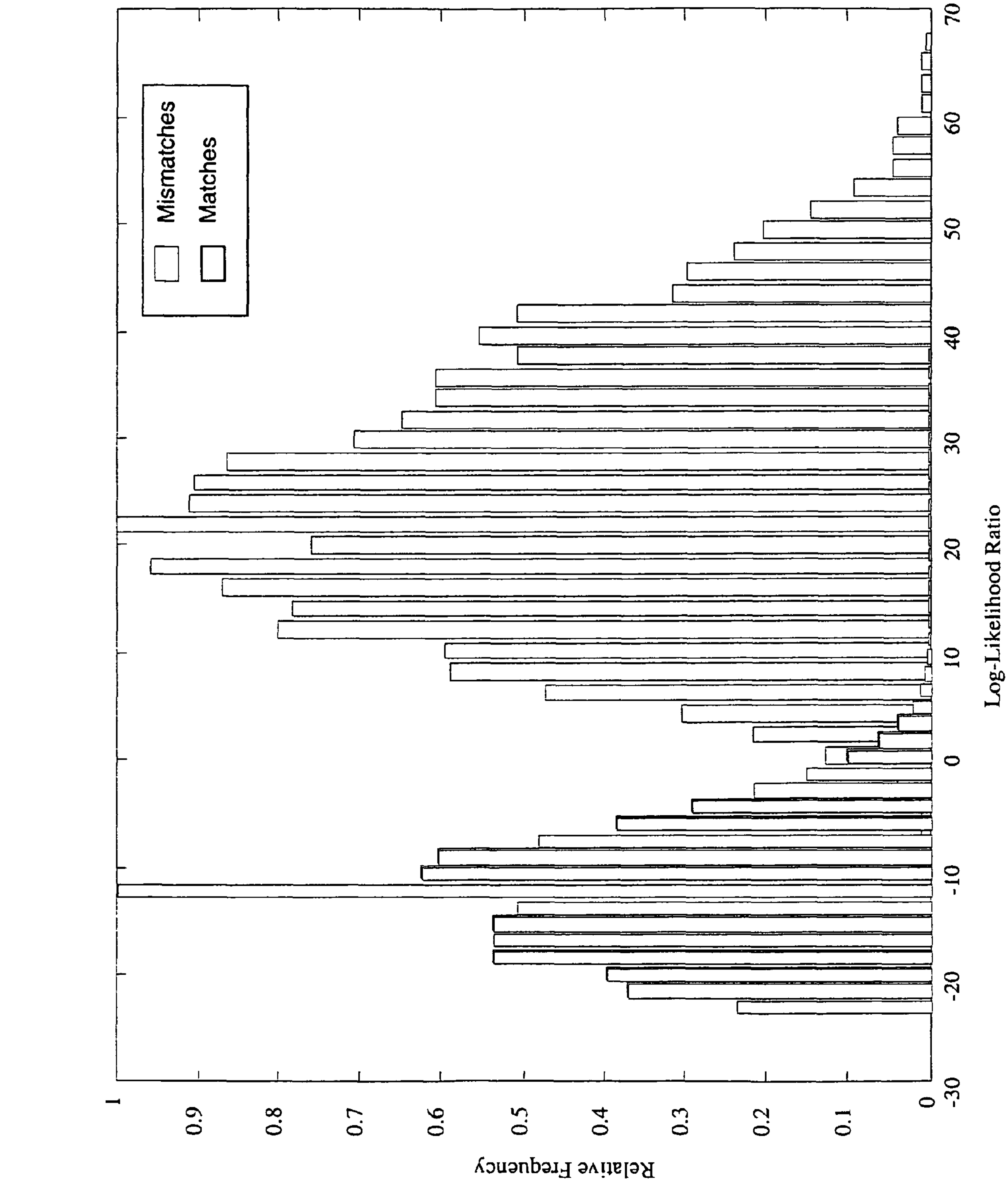
FIG. 5 is a histogram for log-likelihood ratio of comparisons between all test spectra and all fingerprints in an experimental application of the present invention.

To evaluate performance of the proposed peptide scoring algorithm, a critical threshold for the likelihood ratio criterion is selected empirically to be the value that minimizes the false positive and false negative error rates in the test data set. For each data set partition, the false negative rate is reported to be the fraction of spectra that fail to be identified with the correct candidate fingerprint. The false positive rate for each fingerprint set is reported to be the fraction of comparisons that erroneously result in a positive identification. FIG. 4 illustrates the dependence of empirical false positive and false negative probabilities on critical threshold for selected N-mer partitions. A good threshold for each partition is the threshold that minimizes the sum of the false positive and false negative rates, typically near where the false positive line and the false negative line intersect. As seen in FIG. 4, the optimal threshold is typically between one and five for the different N-mer partitions. FIG. 5 plots histograms of the likelihood ratio criterion for comparisons of all test spectra against all candidate fingerprints. Scores for test spectra compared to the correct peptide fingerprint (the matches) are plotted in dark gray, and scores for test spectra compared to the incorrect peptide fingerprint (the mismatches) are plotted in light gray. Ideally, the histograms for the two groups should be distinct and well separated, so a critical threshold can be selected that will produce few or no false positives and false negatives. FIG. 5 shows that the two groups are indeed well separated, however, some overlap is present between −10 and 10. We therefore set the critical threshold to minimize the sum of the false positive and false negative error rates. For this data set, the optimal threshold is 2.3.

TABLE 3

False Negative and False Positive Rates for Peptide Identification using the Likelihood Ratio Criterion with Critical Threshold $K_c$ = 2.3.

| Data | False Negative | False Positive Rate Fingerprint Partition | | | | | | | | | |
|---|---|---|---|---|---|---|---|---|---|---|---|
| Partition | Rate | 6 | 8 | 10 | 12 | 14 | 17 | 20 | 23 | 26 | 30 |
| 6-mers | 0.077 | 0.093 | 0.026 | 0.001 | <0.001 | <0.001 | <0.001 | <0.001 | <0.001 | <0.001 | <0.001 |
| 8-mers | 0.049 | 0.107 | 0.057 | 0.003 | 0.001 | <0.001 | <0.001 | <0.001 | <0.001 | <0.001 | <0.001 |
| 10-mers | 0.044 | 0.064 | 0.053 | 0.009 | 0.003 | 0.001 | <0.001 | <0.001 | <0.001 | <0.001 | <0.001 |
| 12-mers | <0.001 | 0.024 | 0.032 | 0.015 | 0.008 | 0.005 | 0.002 | <0.001 | <0.001 | <0.001 | <0.001 |
| 14-mers | 0.009 | 0.013 | 0.030 | 0.017 | 0.016 | 0.015 | 0.007 | 0.003 | 0.002 | 0.001 | 0.001 |
| 17-mers | 0.004 | 0.004 | 0.015 | 0.012 | 0.018 | 0.019 | 0.016 | 0.010 | 0.007 | 0.004 | 0.004 |
| 20-mers | 0.015 | 0.001 | 0.004 | 0.007 | 0.018 | 0.029 | 0.037 | 0.037 | 0.029 | 0.022 | 0.022 |
| 23-mers | 0.007 | <0.001 | 0.002 | 0.003 | 0.011 | 0.020 | 0.035 | 0.045 | 0.042 | 0.033 | 0.034 |
| 26-mers | 0.016 | <0.001 | <0.001 | 0.001 | 0.005 | 0.010 | 0.020 | 0.035 | 0.036 | 0.033 | 0.038 |
| 30-mers | <0.001 | <0.001 | <0.001 | <0.001 | <0.001 | 0.001 | 0.005 | 0.011 | 0.017 | 0.020 | 0.028 |

Table 3 displays the false positive and false negative error rates (probabilities) using the optimal threshold of 2.3 for the different N-mer partitions. For each data set partition, the false negative rate is reported to be the fraction of spectra that fail to be identified with the correct candidate fingerprint. The false positive rate for each fingerprint set is reported to be the fraction of comparisons that erroneously result in a positive identification. Overall, the results of this approach are promising. Both the false positive and false negative rates are always below ~0.1, and consistently well below 0.05. Interestingly, the error rates are notably highest for 6-, 8-, and 10-mers, and then rapidly decreases as the peptide length increases. There are two possible explanations for this. First, the likelihood ratio tends to be sensitive to the number of peaks in a fingerprint. When only a small number of peaks are being considered in a comparison, the evidence for $H_0$ or $H_A$ tends to be much weaker than when many peaks are being considered. Therefore, short candidate sequences will tend to produce log-likelihood ratios that are near zero where no preference for $H_0$ or $H_A$ is apparent, resulting in relatively larger error rates. Second, the spectra for the shorter peptides tended to contain a disproportionately larger number of peaks than those for longer peptides. This increase in the number of peaks in the spectra increases the chance that an incorrect peptide fingerprint will match the spectrum.

Figure 6:
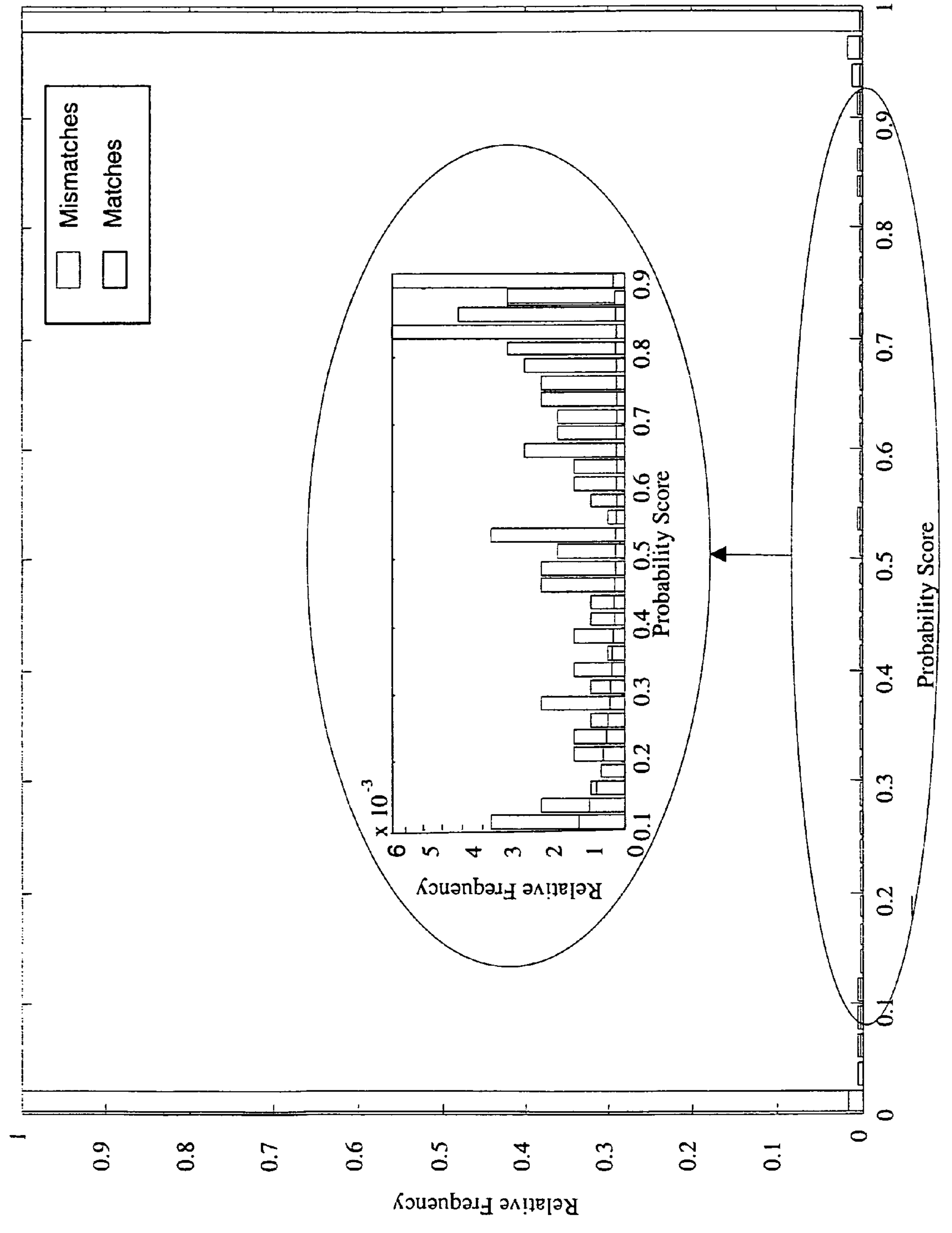
FIG. 6 is a histogram for probability score of comparisons between all test spectra and all fingerprints in an experimental application of the present invention.

FIG. 6 plots histograms of the probability score for comparisons of all test spectra against all candidate fingerprints. As before, scores for test spectra compared to the correct peptide fingerprint (the matches) are plotted in dark gray, and scores for test spectra compared to the incorrect peptide fingerprint (the mismatches) are plotted in light gray. The difference between the histograms in FIGS. 5 and 6 is dramatic. In particular, histograms of the probability score between the two groups are much more distinct than for the likelihood ratio criterion. The probability score for true positives (matches) tends to be very close to one, while the probability score for true negatives (mismatches) tends to be very close to zero. Between 0.1-0.9, a wide region of overlap between the two groups is present, however it involves a small fraction of the test data (relative frequency less than 0.006). These results suggest that the proposed probability score can be a highly effective scoring method for peptide identification.

purely by chance. Conversely, when many candidates are under consideration, the likelihood ratio for a given comparison needs to be large in order to achieve a high probability score for any given candidate. Because of this, it is expected that the probability score will be most conclusive when the number of candidate fingerprints considered is initially reduced as much as possible. This can be achieved, in part, simply by filtering out candidate peptides that do not have a mass consistent with the parent mass observed in the MS/MS spectrum.

Remarks Regarding Peptide Identification

A new approach to scoring sequences for peptide identification using MS/MS data has been discussed. This approach relies on candidate fingerprints whose parameters are constructed from an initial training data set. However, it does not require MS/MS data for each candidate sequence; a fingerprint for any sequence can be constructed once the initial ion offsets and corresponding frequencies have been established. One benefit of some embodiments of the present invention is that it provides a probability score for each comparison. Therefore, interpretation of results is intuitive and can be applied objectively to different data sets without changing decision rules. Another benefit of this approach is that it can be used alone, in conjunction with a database search algorithm, or within a de novo sequencing algorithm.

The disclosed method appears to work effectively and consistently for different peptide lengths. The error rates are highest for short sequences, where the number of biomarkers available for peptide identification is relatively low. For short sequences (10-mer and shorter), the error rate was as high as 10% in this experiment, however, for longer sequences (12-mer to 30-mer), the error rates were significantly lower, typically below 2%-3%. Among 12-mer and longer sequences, comparable error rates are achieved using the same critical decision threshold collected under varied experimental conditions.

TABLE 4

False Negative and False Positive Rates for Peptide Identification Using the Probability Score with Critical Threshold $P\{H_A|x\} = 0.5$

| Data Partition | False Negative Rate | False Positive Rate Fingerprint Partition 6 | 8 | 10 | 12 | 14 | 17 | 20 | 23 | 26 | 30 |
|---|---|---|---|---|---|---|---|---|---|---|---|
| 6-mers | 0.131 | 0.035 | 0.006 | <0.001 | <0.001 | <0.001 | <0.001 | <0.001 | <0.001 | <0.001 | <0.001 |
| 8-mers | 0.187 | 0.041 | 0.017 | 0.001 | <0.001 | <0.001 | <0.001 | <0.001 | <0.001 | <0.001 | <0.001 |
| 10-mers | 0.070 | 0.023 | 0.017 | 0.003 | 0.001 | <0.001 | <0.001 | <0.001 | <0.001 | <0.001 | <0.001 |
| 12-mers | 0.014 | 0.007 | 0.008 | 0.005 | 0.002 | 0.002 | 0.001 | <0.001 | <0.001 | <0.001 | <0.001 |
| 14-mers | 0.027 | 0.003 | 0.008 | 0.005 | 0.006 | 0.006 | 0.002 | 0.001 | <0.001 | <0.001 | <0.001 |
| 17-mers | 0.014 | 0.001 | 0.004 | 0.004 | 0.007 | 0.008 | 0.006 | 0.004 | 0.003 | 0.002 | 0.002 |
| 20-mers | 0.019 | <0.001 | 0.001 | 0.002 | 0.007 | 0.012 | 0.014 | 0.016 | 0.012 | 0.010 | 0.011 |
| 23-mers | 0.011 | <0.001 | <0.001 | 0.001 | 0.004 | 0.007 | 0.012 | 0.020 | 0.019 | 0.016 | 0.018 |
| 26-mers | 0.016 | <0.001 | <0.001 | <0.001 | 0.002 | 0.004 | 0.007 | 0.015 | 0.017 | 0.016 | 0.020 |
| 30-mers | 0.004 | <0.001 | <0.001 | <0.001 | <0.001 | <0.001 | 0.001 | 0.004 | 0.007 | 0.009 | 0.014 |

Analogous to the results presented for the likelihood ratio criterion, Table 4 displays the false positive and false negative error rates (probabilities) for the different N-mer partitions when probability score is used for peptide identification. In this case, no optimal probability score is computed. Rather, the critical threshold for positive identification is arbitrarily set to 0.5 so that $P\{H_A|x\}>0.5$ results in a positive identification and $P\{H_A|x\}\leqq 0.5$ results in a negative identification. Interestingly, the false negative rate is consistently higher and the false positive rate is consistently lower when using the probability score than those obtained when using the log-likelihood ratio criterion. When many candidates are under consideration, the probability score will tend to be low due to the likely scenario of one or more high likelihood ratios In some embodiments, the method discussed above is used to identify non-tryptically digested peptides and peptides of varying charge. In other embodiments, this scoring method might be used in conjunction with complementary methods to improve its ability to perform peptide identification. Other applications and modifications will occur to those skilled in the art. For example, ion offset frequencies used in candidate fingerprints tend to be overestimates, since the frequencies are computed using counts observed at each offset without considering the number observed purely by chance. In another example, mathematical models may be used to provide ion type frequencies that estimate frequencies for peptide sequences for which experimental data are not available. In addition, the probabilistic model presented here assumes the different fingerprint peaks appear independently of one another, which may be unrealistic (in the case of the y- and b-series ions, for example). Extension of the probabilistic model and disclosed method to include more realistic assumptions may be realized without department from the present invention.

Genetic Algorithm for Peptide Analysis

Peptide identification following tandem mass spectrometry is usually achieved by searching for the best match between the mass spectrum of an unidentified peptide and those available in a database. This methodology will be successful only if the peptide under investigation belongs to an available database.

The method now to be discussed uses a Genetic Algorithm (GA) to reconstruct amino acid sequences of peptides using only spectral features. The GA can potentially overcome some of the problems associated with real MS/MS data like incomplete or unclearly defined peaks, and may prove to be a valuable tool in the proteomics field. The performance of this algorithm under conditions of perfect spectral information, and also in situations where some spectral features are missing, are discussed below.

Context of GA Application to Peptide Identification

Determining the correct sequence of amino acids for a peptide starting with MS/MS spectral data can be stated as an optimization problem where the objective is to match an experimental spectrum with the amino acid sequence most likely to produce it.

In general, two approaches have been proposed for the solution of this problem. In the first, the MS/MS spectrum of an unknown peptide is compared to idealized spectra derived from genomic databases (Eng, McCormack et al. 1994;). The best match, or matches, are reported as answers. This method will fail to identify a correct peptide if the peptide sequence under investigation is unavailable in the search database. This can happen for a number of reasons, including differences in the genomes of the organism studied in the field and the one which was sequenced, frameshifts that occur during translation, alternative splicing, and post-translational modifications.

The second approach attempts to find an amino acid sequence that would produce the spectrum at hand without referring to an archive of previously available peptide sequences. This de novo methodology uses only the peaks in the spectrum to deduce the sequence of amino acids that gave rise to it and is usually stated in a graph-theoretical framework (Taylor and Johnson 1997; Dančik, Addona et al. 1999). The objective in this problem is to create a sequence of amino acids that helps explain the most important spectral features observed.

Consider a peptide formed by the amino acid sequence SEQ ID NO: 2 (LFSQVGK). A complete and perfect fragmentation of this peptide into singly charged b- and y-ions would produce peaks at the positions shown in FIG. 7. For simplification purposes, we assume that all ions are detected and all have the same relative abundance. The information contained in FIG. 1 can be used to reconstruct the original peptide because the difference (in mass/charge, or m/z, units) between adjacent peaks of a given ion type corresponds to the mass of an amino acid residue in the original sequence. If a fragmentation occurs at every amino acid and every resulting fragment is detected as a singly-charged ion, the problem of reconstructing the peptide using spectral information is greatly simplified and can be solved efficiently using dynamic programming methods (Dančik, Addona et al. 1999).

Unfortunately, experimental results are seldom this perfect and the researcher is confronted with spectra that contain missing or unclearly defined peaks. Real spectra may also show peaks from a variety of other peptide fragments as well as considerable background noise. Departures from perfect behavior make the computationally efficient dynamic programming algorithms lose their edge when dealing with real spectral data.

Even if perfect information is available, the graph-theoretical approaches require unambiguous identification of all spectral features (all peaks must be assigned to a certain type of ion) to produce the correct answer. This assignment is clearly not an easy task. In the absence of clear identification, there is no guarantee that the graph-theoretical methods will produce the correct answer.

In the present example embodiment, a GA is used to solve the de novo sequencing problem. Genetic Algorithms have become an increasingly popular methodology to solve difficult combinatorial optimization problems in many different areas of science and engineering. The term Genetic Algorithm (or GA) is used whenever a small group of potential solutions is evolved until some criterion of convergence has been reached. The main idea behind GA is that, by combining small blocks of relevant information, good solutions can be created. The solutions generated in a run have, potentially, the ability to explore any portion of the entire problem space. Since GA only require the assignment of a goodness value to any given solution, they are not deterred by discontinuities in the search space, noisy objective functions or non-linearly constrained spaces. The following sections present a brief explanation of how a GA can be employed to solve it.

SYSTEMS AND METHODS

General Approach

Although numerous different implementations exist, a typical GA consists of the following elements: encoding, generation of an initial population, evaluation, recombination, selection and mutation.

Solutions to the problem (in our case a sequence of amino acids that make up a given peptide) are encoded as strings of characters. These strings (also called individuals or chromosomes) should be flexible enough to assign a unique representation to every possible solution to the problem. Binary encoded individuals (1/0) have been the traditional choice in many GA applications but other representations can also be used.

Using an appropriate encoding, a relatively small number of individuals are created to start the run. Generally, this population consists of some 20-50 chromosomes. Variety in the contents of the initial population is usually more important than the quality of the individual solutions themselves.

Each chromosome must be evaluated with respect to one or more objectives and a fitness value (the terms objective value, fitness and score are used interchangeably herein) assigned to it. The fitness of each individual is usually, but not necessarily, represented by a single real number.

The available population of chromosomes is used to build new solutions, generally by breaking two of them apart and putting the resulting portions together in a way that differs from either parent. The recombination (or mating) procedure allows the exploration of the space spanned by the individuals in the current population.

After a relatively large group of new solutions has been created using the recombination mechanism, the new chromosomes are evaluated. Those with better fitness values are chosen to form part of the new parent generation at the expense of the rest. Since the size of the parent population is a fraction of the number of offspring individuals, competition for the available spots forces gradual improvements in the overall fitness of the evolving population.

A few individuals in the new parent generation have some, or all, their contents altered. This ensures that all the information needed to solve the problem remains available for the construction of new solutions. The mutation mechanism provides resources to expand the search into unexplored regions of the problem space.

Specific Approach for MS/MS Data

This exemplary implementation of our algorithm starts with a small initial population of potential amino acid sequences, generated completely at random. The purpose of this initial population is to provide the algorithm with building blocks of useful information that can be combined in ways that, hopefully, allow it to construct better solutions. We do not impose any requirements on the contents of the initial population. The length of these first chromosomes can be kept within a reasonable range of values. This range does not have to be very strict since our procedure allows the individuals to increase or decrease in length throughout the procedure. For the purposes of this example, initial solutions have lengths that vary randomly between three and ten amino acids. An instance of an initial population is shown in Table 5.

TABLE 5

| Initial Population in Example Application | |
|---|---|
| SEQ ID NO: 3 | (VQSGKMG) |
| SEQ ID NO: 4 | (FSQDMYVQR) |
| SEQ ID NO: 5 | (NEWANNSQR) |
| SEQ ID NO: 6 | (VQSR) |
| SEQ ID NO: 7 | (RQSTCARFSF) |
| SEQ ID NO: 8 | (TDSCTVQVCW) |
| SEQ ID NO: 9 | (WRSGDPMLQF) |
| SEQ ID NO: 10 | (DSNKKCGTNE) |
| SEQ ID NO: 11 | (AELQNCRKQF) |
| SEQ ID NO: 12 | (CMNPRFESLQ) |
| SEQ ID NO: 13 | (FWSTDAHKPL) |
| SEQ ID NO: 14 | (PVLSYSEETH) |
| SEQ ID NO: 15 | (SWRLMWQKKF) |
| SEQ ID NO: 16 | (QNNEFQMCDV) |
| SEQ ID NO: 17 | (NCGFQNSMDD) |
| SEQ ID NO: 18 | (CHKLNTPFSH) |
| SEQ ID NO: 19 | (FFCVDYTPRH) |

TABLE 5-continued

| Initial Population in Example Application | |
|---|---|
| SEQ ID NO: 20 | (NRVAVNFCTP) |
| SEQ ID NO: 21 | (LQHECVNGLY) |
| SEQ ID NO: 22 | (FYGNGRPGLK) |

Next, we proceed to the recombination step. Two sequences are selected at random from the available population and a breaking (or crossover) point chosen, also at random, in each of them. For example, from the initial population shown in Table 5 the two individuals SEQ ID NO: 8 (TDSCTVQVCW) and SEQ ID NO: 6 (VQSR) are chosen and a random crossover point is selected.

(8)

SEQ ID NO: 8 (TDSC | TVQVCW)

SEQ ID NO: 6 (VQ | SR)

The new sequence is formed by adjoining alternate portions of the parent individuals:

(9)

SEQ ID NO: 23 (TDSCSR)

The new sequence differs from either parent not only in its contents but also in length. This step gives the procedure flexibility for constructing candidate peptide chains that are widely different from the ones available in the current population, allowing the exploration of a relatively large and varied portion of the problem space. The mating procedure is repeated until the number of new sequences equals five to seven times the size of the initial population. Increasing the number of individuals created in the recombination procedure has the effect of performing a more thorough exploration of the material available in the current population. The mating mechanism we have presented here can be easily modified to allow the participation of more than two parent individuals in the creation of a new chromosome and multiple crossover points in every mating event.

The newly created individuals are evaluated with respect to one or more objectives (discussed below) and the ones with better overall fitness are selected to become the new parent generation. These new parents are then mutated according to a very simple procedure. A small percentage of them (generally 5 to 15%, but a higher percentage is not uncommon) have some of their contents altered. Assume that the sequence that was created in the recombination step is chosen for mutation. Some possible mutation mechanisms include random replacement of amino acid residues in the selected individual:

(10)

SEQ ID NO: 23 (TDSCSR) → SEQ ID NO: 24 (TDSKMR), insertion of new residues, (11)

SEQ ID NO: 23 (TDSCSR) → SEQ ID NO: 25 (TGDSCVYSR)

or inversion of existing peptide portions (12)

SEQ ID NO: 23 (TDSCSR) → SEQ ID NO: 26 (TSCSDR)

Notice that the last mutation strategy (inversion) does not bring any new material into the existing population and may result in premature convergence if it is not supplemented by some combination of the other mutation mechanisms.

Development of the Fitness Function

Up to this point we have avoided discussion of the fitness evaluation. In most optimization problems, the objective, or objectives, can usually be clearly stated either as mathematical functions or some combination of rules to be followed or decisions to be made under appropriate circumstances. In the case of MS/MS spectra, all we know is that the end result should be a complete sequence whose weight and main spectral features match that of the experimental peptide. The matter of how these objectives will be achieved using the available spectral information is by no means a solved problem.

There are several ways in which a fitness function can be created for this problem. If we guide the evolving candidates by the weight of the experimental peptide only, we will likely obtain an erroneous sequence of amino acids with a total weight that is very close to that of the target. To decrease the chances of converging to an incorrect sequence, spectral peaks can be used as a guide during the search. A peptide sequence that results in a simulated spectrum similar to the experimental one should be given more consideration than one which produces features that do not resemble those we are interested in.

To produce a simulated spectrum for a candidate sequence in this exemplary embodiment we proceed as follows. The candidate chain is broken up, from left to right, one amino acid at a time. This generates two peptide fragments, and any one of them could be detected as a singly charged species (we consider singly charged product ions only). We will assume for demonstration purposes that the dissociation of a peptide results in only two types of fragments, b- and y-ions. For example, the protein created in the recombination step would be first broken up into:

T and SEQ ID NO: 27 (DSCSR) (13)

which would produce two simulated peaks, one at 101+1=102 m/z units and the other at 540+17+2=559 m/z units. The former peak represents the nominal residue mass of threonine with an additional proton on the N-terminus. This fragment has a charge of +1. (In practice, this $b_1$ ion does not form but is used here for demonstration purposes.) The latter peak with an m/z value of 559 represents a y-ion fragment. The corresponding mass value consists of the nominal value of the sum of the residue masses for SEQ ID NO: 27 (D S C S R) with the addition of a C-terminal hydroxy group, a proton on the N-terminus to form the amine, and an additional proton on the side chain of the C-terminal arginine. Each peak in the experimental spectrum that is also present (within certain tolerance) in the simulated spectrum can be counted as a match. In this work, we count a match if a simulated b- or y-ion is within 0.01 of an m/z unit of a peak in the target spectrum. This level of tolerance is very strict and will surely prove inappropriate for some experimental conditions but we chose to use it to avoid situations where the number of distinct combinations of amino acids that could be matched to the same peak were so numerous as to render the procedure useless.

Fragmenting the peptide after the second amino acid produces a second set of simulated peaks:

TD and SEQ ID NO: 28 (SCSR) (14)

The process continues until fragmentation occurs between all adjacent amino acids in the sequence. To create a very simple fitness function we can increase a peak counter every time a peak in the target spectrum matches one of the simulated ones and decrease it if an experimental peak cannot be found among the simulated ions. Notice that our procedure for simulating the spectrum of a potential solution considers only clean cleavages between the carboxyl carbon of one amino acid and the amino nitrogen of the next. These b- and y-ion fragments are the most common product ions in ion-trap mass spectrometers (Kinter and Sherman 2000, cited above). Simulation and matching of peaks produced by other ion types could be incorporated in the evaluation procedure at the cost of a modest increase in the number of computations involved.

A second term in the fitness function, dealing with total peptide weight, can be made to work in a similar but much simpler way. The total mass of the precursor peptide is the sum of the residue masses of the amino acids in the chain plus 17 Da for a C-terminal hydroxy group, 2 Da for the N-terminal amine, and an additional proton on the side chain of the C-terminal arginine or lysine in the case of tryptic peptides. Sequences are penalized for deviations on either side of the target weight. The severity of this penalization can be easily modified to influence the behavior of the algorithm around the target weight. The one we used is shown later on in this section.

At this point, the terms in the objective function can account for spectral similarities and total weight. These elements can determine if a given sequence resembles the target one but they alone cannot make the GA work. The reason for this lies on the fitness landscape that results when using an objective function made up exclusively by these terms. The fitness landscape is a map of the objective function as values of the independent variables change through the feasible space. Let's examine what would happen during a run of the GA using an objective function that includes the terms we have described so far. Suppose that our input consists of the spectrum shown in FIG. 7 (an ideal spectrum of the sequence SEQ ID NO: 2 (LFSQVGK)) and the mass of the complete peptide (778.91 Da). For convenience in this example our objective function will be stated simply as:

$$\text{fitness} = w_1 \cdot \sum(\text{matching peaks}) - w_2 \cdot \sum(\text{non matching peaks}) + \frac{w_3}{1 + |\text{weight} - \text{target}|} \quad (15)$$

where $w_1$, $w_2$ and $w_3$, are empirical constants whose magnitude can be adjusted to alter the relative importance of every term in the fitness function. To simplify matters in this example, these constants are all equal to one. It should be apparent that higher fitness values are associated with sequences whose spectra match the experimental peaks well and have molecular weight close to the target. Using this objective function, the correct peptide sequence has a fitness value of:

fitness(SEQ ID NO: 2 (LFSQVGK)) = 12 − 0 + 1 = 13 (16)

The GA will attempt to find the correct amino acid sequence using pieces from randomly generated peptides and we expect that better fitness values will be associated with sequences that closely resemble the one that produced the experimental spectrum. This does not occur with the fitness function described above. Consider the sequence SEQ ID NO: 29 (LGSQVGK). This peptide is almost identical to the one we are looking for; with the only difference in the Glycine in place of the Phenylalanine at the second position as we read the chain from left to right. We should expect that this sequence would have very high fitness but, in fact, the objective function value for this chain is:

fitness(SEQ ID NO: 29 (LGSQVGK)) = 6 − 6 + 0.011 = 0.0110 (17)

The fitness of the modified sequence is less than 0.1% that of the correct peptide and all three terms in the objective function have changed considerably (for the worse) compared to their optimal values. Now consider, for comparison purposes, the sequence SEQ ID NO: 30 (APAHVVGK). This peptide resembles the one we are looking for only at one end and it is clear that it would be necessary to modify it considerably before arriving at our target peptide. Despite the lack of similarity between SEQ ID NO: 30 (APAHVVGK) and SEQ ID NO: 2 (LFSQVGK), the fitness of the new peptide is:

fitness(SEQ ID NO: 30 (*APAHVVGK*)) = 6 − 6 + .0384 = .0384 (18)

By considering number of matching peaks and total weight only, the fitness of this new peptide is more than three times that of one nearly identical to the target. The implications of this for the behavior of the GA, or other search procedures employing a similar objective function, are severe. The GA would quickly divert resources away from the nearly correct sequence and towards the one with higher fitness value. Under these circumstances, our search procedure would have virtually no chance of converging to the correct amino acid sequence.

Figure 8:
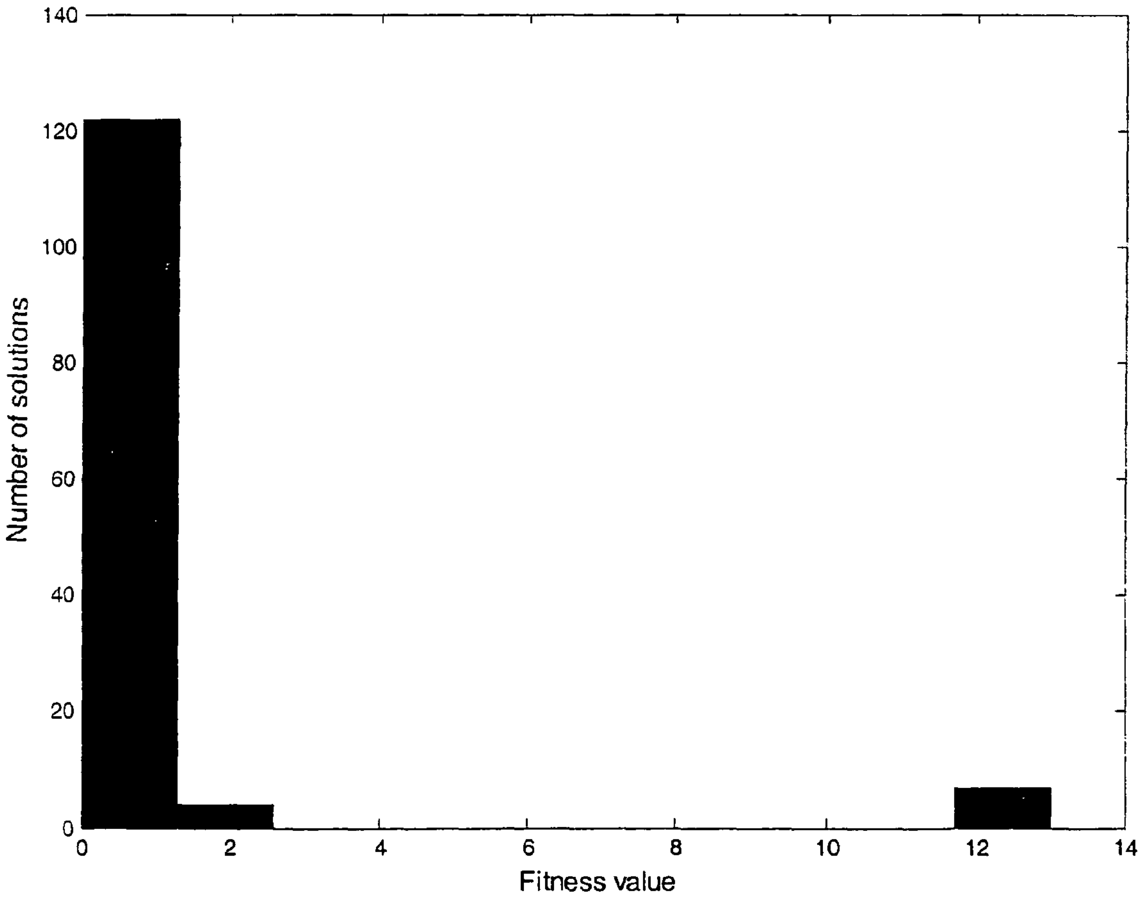
FIG. 8 is a histogram of fitness values obtained in one application of the genetic algorithm-based embodiment of the method of the present invention.

To get a better idea of the changes in the fitness function whenever a single amino acid is substituted by another in the SEQ ID NO: 2 (LFSQVGK) sequence, we present, in FIG. 8, a histogram of fitness values as every amino acid in the chain is replaced by each of the 19 residues available (notice that we include cases where an amino acid is replaced by itself, that there are only 19 amino acids to choose from since we cannot distinguish between L and I and that the sequence resulting from the substitution will differ from the original one by at most one amino acid). The majority of the substitutions reduce the fitness value to practically zero (more dramatic changes in the peptide sequence could result in negative fitness values). Fitness is not reduced any further because changing any one amino acid in the correct peptide chain cannot result in anything less than six matching peaks and, consequently, no more than six non-matching peaks.

FIG. 8 shows that peptides that are structurally very similar to the one that produced the ideal spectrum score very poorly with the current objective function. In fact, these highly similar peptide sequences may score worse than sequences that are not at all like the target one. Since the GA uses only the value of the objective function to decide which individuals survive the selection step, it is almost certain that the procedure we have described so far will converge to an incorrect sequence as the final answer.

The problem of finding an optimum objective function value in a landscape that is relatively flat except for a single optimal point in the feasible space can be notoriously difficult to solve due to the lack of useful guiding information available. Despite its good characteristics, the GA will be of no help in a problem where solutions that are nearly identical with the optimum score similarly—in fitness value—than those that are very different.

A modification to the objective function that takes similarity of peptides into consideration is necessary to make the GA work. Efforts to derive similarity measures among mutated and modified peptides have been presented in the art. The present embodiment illustrates a methodology to measure peptide similarities analogous to the cited references, but one that is adapted specifically for the GA.

Consider an experimental spectrum whose m/z values can be described as a set of m peaks $S=\{s_1, s_2, s_3 \ldots S_m\}$ (possibly consisting of more than b- and y-series ions) and the simulated spectrum of a potential solution, $P=\{p_1, p_2, p_3 \ldots p_n\}$ (b- and y-series ions only), as a set of n peaks. Computing the differences between every peak in P and every peak in S results in an n by m matrix of differences $D=\{d_{ij}=(s_i-p_j)\}$, $1 \leqq i \leqq m$ $1 \leqq j \leqq n$ whose entries can be inspected to find those peaks in P that, if translated, would match peaks in S. If every entry in D has a distinct numerical value, it is not possible to exactly match more than one peak between P and S simultaneously by adding a single real number to all the entries of either spectrum. On the other hand, if multiple entries in D have the same numerical value (within a given tolerance), these represent peaks in P that—either in their original position or after an appropriate shift—can be made to match peaks in S. The multiplicity of repeated entries in D can be used as an indication of the similarity between S and P.

Others have considered cases where the shifts needed to match peaks between two spectra could be traced to the substitution of one or two amino acid residues in the target peptide chain. This procedure of spectral alignment is based on a dynamic programming algorithm where both spectral peaks and the masses of amino acids are approximated by integers. The procedure considers only ions in the b-series since simultaneous use of b- and y-series ions (or other types of ions) can make the dynamic programming algorithm converge to infeasible solutions. In our case, we are not interested in finding a particular amino acid substitution that can be used to explain all the differences between two spectra. Rather, our aim is to use the number of repeated entries in D to help us assess the relative fitness of potential solutions to our problem. This is achieved by adding a term to the objective function that determines whether two or more peaks in the simulated spectrum of a potential solution can be matched to those in the target spectrum by an appropriate translation.

The new term in the objective function is computed as follows. Given spectra for the target and a potential solution, entries in D are computed and stored as elements in a list. The number of peaks that could be matched between the potential and actual spectra by a translation is the number of non-distinct numerical entries in D (again, within a given tolerance). Notice that this new fitness function term increases in value only if at least two peaks can be simultaneously matched by a translation and that a given peak could contribute to more than one translated matching. The number of peaks that can be made to match by translation can be incorporated into the fitness function as a fourth adding term:

$$\text{fitness} = w_1 \cdot \sum \text{match\_peaks} - w_2 \cdot \sum \text{non\_match\_peaks} + \frac{w_3}{1 + |wt - \text{target}|} + w_4 \cdot \text{transl\_matching\_peaks} \tag{19}$$

where $w_4$ is an appropriately chosen weighing constant. Of the four terms in the objective function, the ones counting non-matching peaks and deviations from the target weight make this a penalty-guided search so that infeasible solutions do not have to be discarded immediately and may in fact be kept throughout a run. This is important since our building procedure does not assume that the correct sequence can be assembled in a single try or using only feasible alternatives.

The values of the constants $w_1$ through $w_4$ should be carefully chosen. As we have defined the terms in the fitness function, it is possible for an incorrect amino acid sequence to have a larger number of peaks that could be matched by translation than the true sequence. An incorrect sequence could also produce a simulated spectrum that matches more peaks in the target than those matched by the simulated spectrum of the true amino acid sequence. This can happen if the target spectrum contains many peaks produced by a variety of ion types (or even background noise). In this case, the spectrum of an incorrect peptide can find a potentially large number of matches with some of the extraneous peaks present in the target while the simulated spectrum of the correct sequence may have fewer matching peaks. The terms we have selected for inclusion in the fitness function will serve as rough indicators of similarity between potential sequences and the target spectrum. This combination of objectives will in many instances help the GA to converge gradually to the correct sequence, and amino acid sequences that closely resemble our objective will have better fitness values than completely unrelated ones. Also, unless the target spectrum is badly contaminated with noise or missing sizeable portions of relevant data, the correct amino acid sequence is likely to be among the highest scoring peptides that can be found.

Consider again the two sequences we discussed before, SEQ ID NO: 29 (LGSQVGK) and SEQ ID NO: 30 (APAHVVGK). Computing the number of non-distinct peak entries in the matrix D for each of these sequences, we obtain:

```
                                                      (20)
# non_distinct D entries(SEQ ID NO: 29
(LGSQVGK)) = 60
# non-distinct D entries(SEQ ID NO: 30
(APAHVVGK)) = 29
```

The number of non-distinct entries in the matrix D is the number of peaks that can be matched by an appropriate translation in the two spectra under consideration. Observing the values of this new term, it is clear that the first of the two sequences has a greater similarity with the target spectrum than the second one. We will make use of the behavior of this count of non-distinct peak locations to help us during the GA search.

Figure 7:
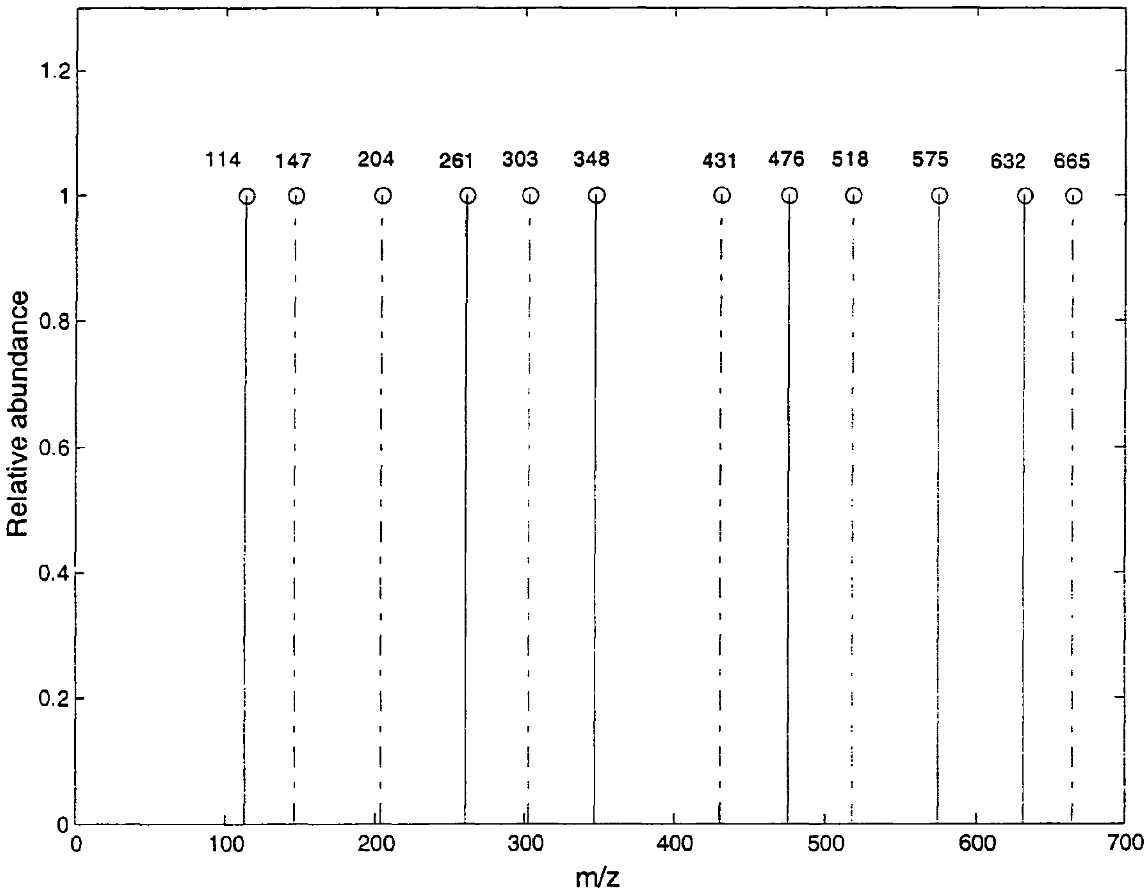
FIG. 7 is an ideal spectrum of the sequence SEQ ID NO: 2 (LFSQVGK) for use with one embodiment of the present invention.
Figure 9:
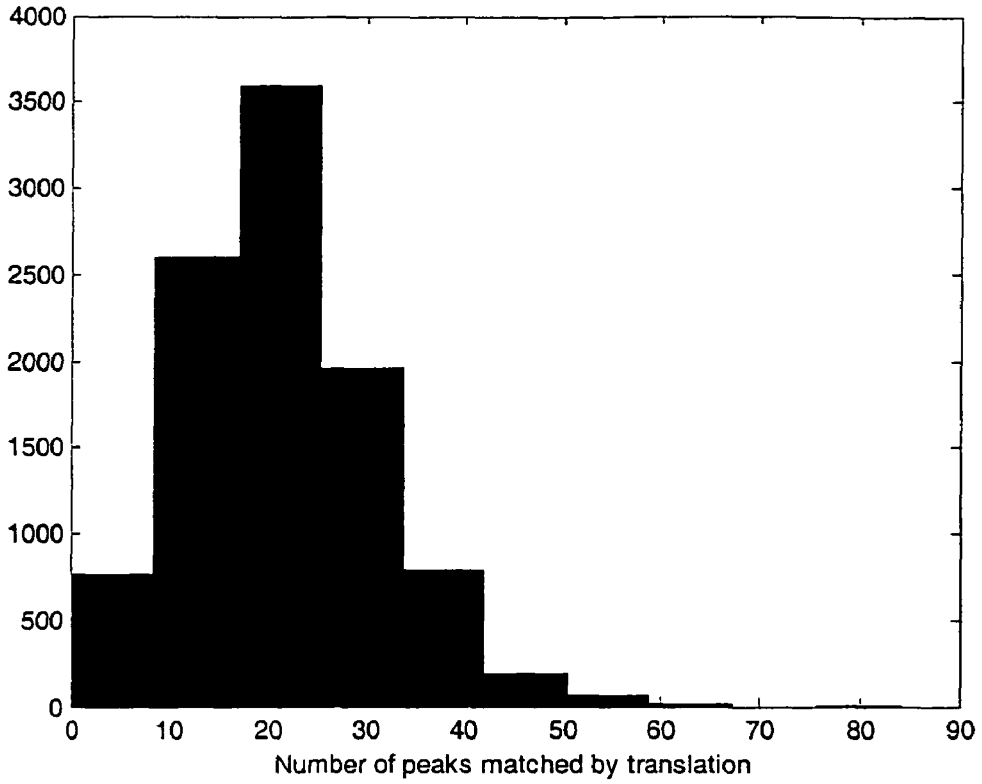
FIG. 9 is a histogram of the number of peaks that could be matched by a translation for selected sequences and the target spectrum from FIG. 7 by application of one embodiment of the present invention.

As a simple test of the potential usefulness of this new term, a histogram of the number of peaks that could be matched by a translation for 10,000 independently generated random amino acid sequences (with length between 7 and 10 each) and the target spectrum in FIG. 7 is shown in FIG. 9.

Figure 10:
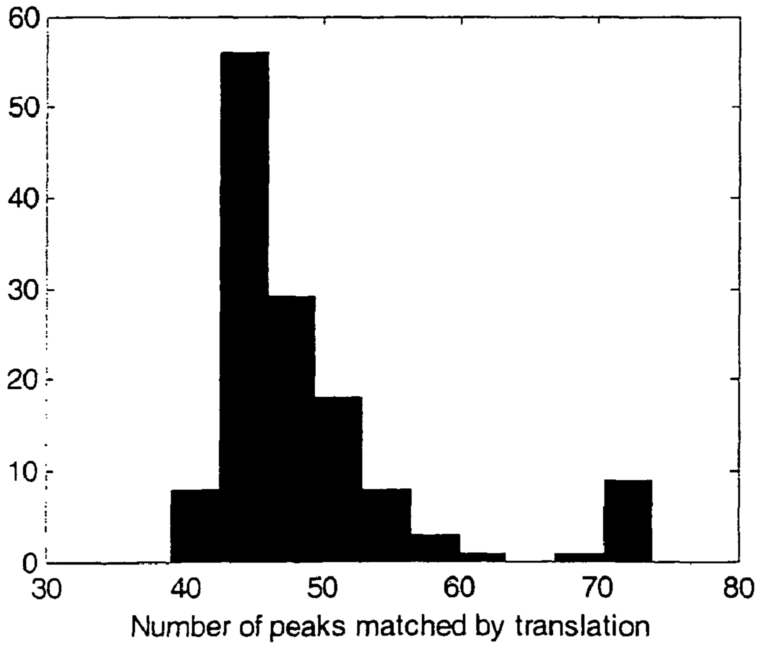
FIG. 10 is a histogram of the number of non-distinct entries in matrix D when comparing the idealized spectrum of FIG. 7 with the hypothetical spectrum produced by one amino acid substitution relative to the sequence SEQ ID NO: 2 (LFSQVGK).
Figure 11:
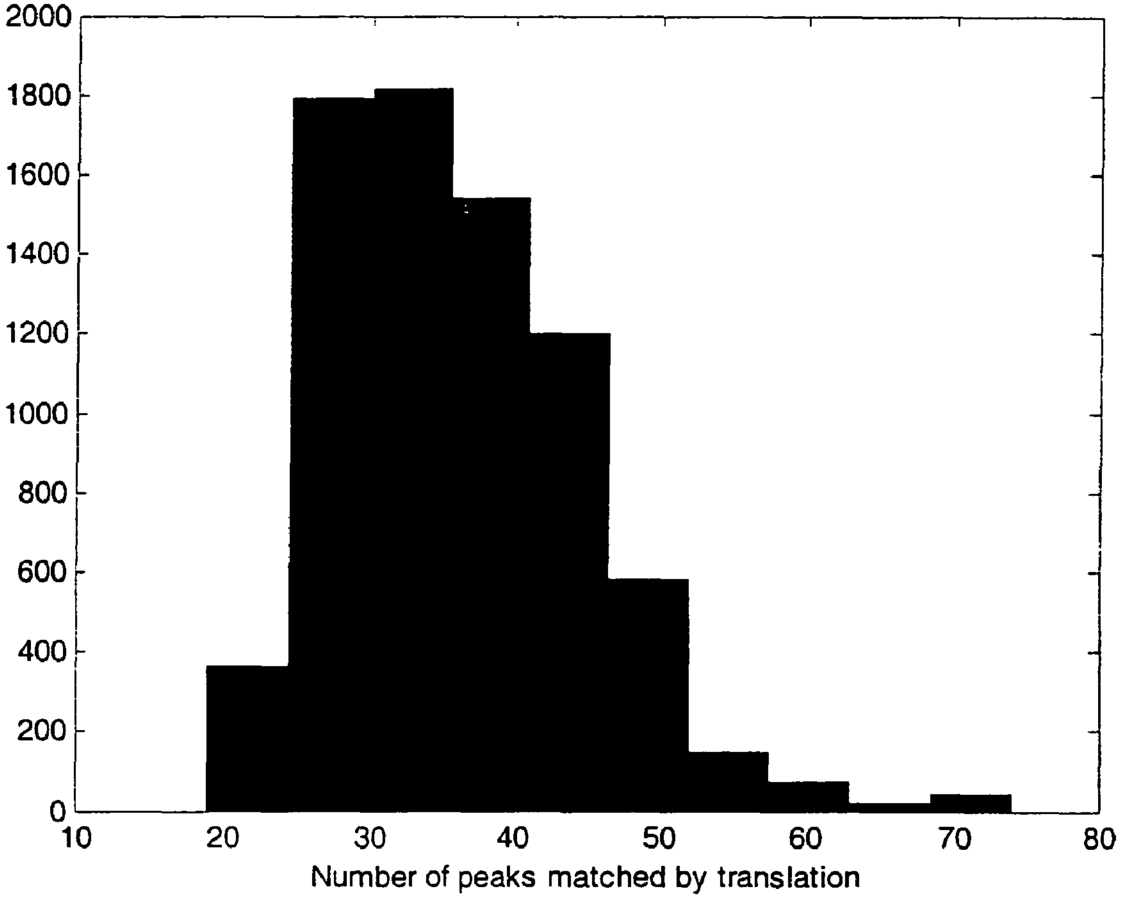
FIG. 11 is a histogram of the number of non-distinct entries in matrix D when comparing the idealized spectrum of FIG. 7 with the hypothetical spectrum produced by two amino acid substitutions relative to the sequence SEQ ID NO: 2 (LFSQVGK).
Figure 12:
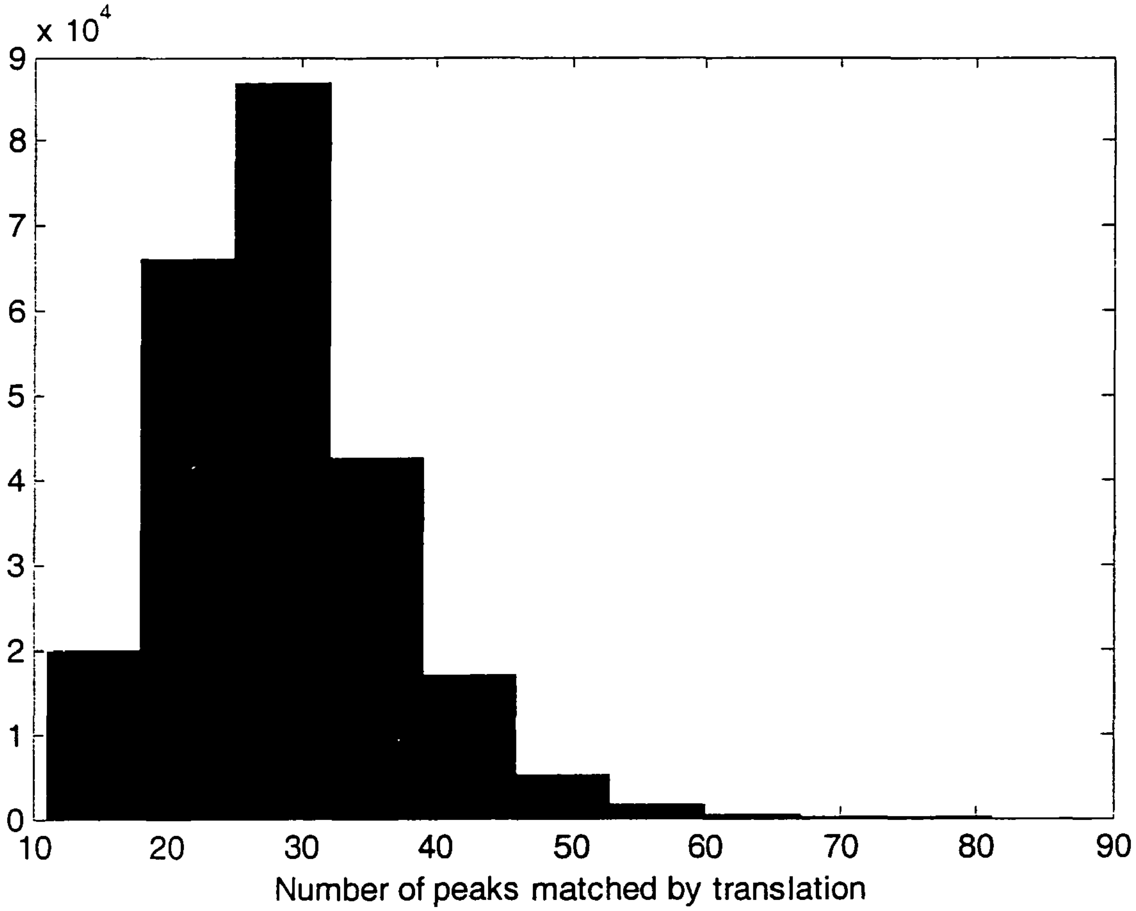
FIG. 12 is a histogram of the number of non-distinct entries in matrix D when comparing the idealized spectrum of FIG. 7 with the hypothetical spectrum produced by three amino acid substitutions relative to the sequence SEQ ID NO: 2 (LFSQVGK).

The vast majority of the random sequences have a number of non-distinct entries in D of 30 or less. For this information to be useful, we need to show that sequences that are similar to the one we are looking for have a distribution of non-distinct entries of D that differs significantly from that of random ones. Histograms of the number of non-distinct entries in D obtained when comparing the idealized spectrum of FIG. 7 with the hypothetical spectra produced by one, two and three amino acid substitutions relative to the sequence SEQ ID NO: 2 (LFSQVGK) are shown in FIGS. 10, 11, and 12, respectively.

The evolution of these figures indicates that significant alterations to the original peptide sequence must be done before the distribution of peaks in D resembles that of randomly generated amino acid chains. Now we would like to see if the inclusion of this new term in the fitness function could help us reconstruct the correct peptide sequence. To this end, we employ a series of runs with two different scenarios:

1. Perfect information. The full spectrum in FIG. 7 is used as the target (using m/z values only, that is, no intensity information is employed). The objective of this first set of runs is to establish the reliability of our algorithm in finding the correct answer when no spectral information is missing. One thousand independently started runs are made. This relatively large number of runs is used to estimate the true rate of correct answers produced by the algorithm. We do not intend to employ these many runs under practical circumstances.
2. Missing peaks. One or two peaks in the original spectrum are deleted and the algorithm executed as above. Ten independently started runs are made after every deletion of spectral features. This number of runs presents the user with a reasonable and realistic option in the amount of computing resources spent.

Other parameters for the optimization are as follows. The size and make-up of the initial population was 50 randomly generated sequences with 7-10 amino acids each. From these initial 50 sequences, 350 individuals were created during the recombination procedure using up to three different parent chromosomes and up to four crossover points for every offspring individual. The best 40 solutions in the newly created offspring population are selected to create new parent generation and supplemented by ten more individuals generated at random. As a result, the parent population has 50 individuals in all generations. Up to 55% of the new parent individuals could have some (or all) their contents altered by random amino acid substitutions including the possibility of substituting an amino acid by itself. The recombination, selection and mutation procedures are followed for 150 generations. The target in this case is the complete perfect spectrum used in FIG. 7 consisting of the set of peaks {114.16, 147.18, 204.23, 261.34, 303.36, 348.42, 431.49, 476.55, 518.57, 575.68, 632.73, 665.75}. The target mass of the full-length peptide was 778.91 Da, which is the m/z of the precursor peptide (389.46) multiplied by a charge of 2.

The values of the weights in the fitness function were selected by running a simple $2^4$ full factorial experiment with four center runs and using the complete spectrum in FIG. 7 as the target. Ten independently started GA runs were made for each of the 20 experiments using as the response of interest the number of times that the correct sequence was obtained in those ten runs. Based on the results from the experiment, we set $w_1=1$, $w_2=1$, $w_3=1$, $w_4=20/|D|$ where $|D|$ represents the number of elements in the matrix D. One may use designed experiments for parameter optimization, as is known in the art.

Results and Discussion

Out of the 1000 independently started runs with perfect information, the correct sequence was found at the end of 384 of them. These 384 correct sequences were also the highest scoring solution among all 1000. Whenever the sequence reported as answer did not correspond to SEQ ID NO: 2 (LFSQVGK), it did have most of its contents in agreement with the correct peptide. For example, the second highest-ranking sequence (after, the correct peptide) was SEQ ID NO: 31 (LFSGAVGK). This sequence has the exact same molecular weight (to two decimal places) as the target peptide because the sum of residual masses of Glycine and Alanine add up to 128.13 Da, the same total mass as the Glutamine residue, the correct amino acid for that position in the chain. The SEQ ID NO: 31 (LFSGAVGK) peptide does not score as high as the correct peptide because its simulated spectrum does not result in as many matching similarities (as counted by examining the number of non-distinct entries in the matrix D) as the correct chain. A summary of the target peaks matched by ions in the b- and y-series for the top two scoring sequences are shown in Table 6 and Table 7 respectively.

TABLE 6

Target Peaks Matched by Ions in the b- and y-Series for Candidate SEQ ID NO: 2 (LFSQVGK)

| Spectrum for: | SEQ ID NO: 2 LFSQVGK | Target Spectrum | Matches |
|---|---|---|---|
| | 114.1 | 114.1 | X |
| | 147.1 | 147.1 | X |
| | 204.2 | 204.2 | X |
| | 261.3 | 261.3 | X |
| | 303.3 | 303.3 | X |
| | 348.4 | 348.4 | X |
| | 431.4 | 431.4 | X |
| | 476.5 | 476.5 | X |
| | 518.5 | 518.5 | X |
| | 575.6 | 575.6 | X |
| | 632.7 | 632.7 | X |
| | 665.7 | 665.7 | X |
| Total | | | 12 |
| Total non- | | | 0 |

TABLE 7

Target Peaks Matched by Ions in the b- and y-Series for Candidate SEQ ID NO: 31 (LFSGAVGK)

| Spectrum for: | SEQ ID NO: 31 LFSGAVGK | Target Spectrum | Matches |
|---|---|---|---|
| | 114.1 | 114.1 | X |
| | 147.1 | 147.1 | X |
| | 204.2 | 204.2 | X |
| | 261.3 | 261.3 | X |
| | 303.3 | 303.3 | X |
| | 348.4 | 348.4 | X |
| | 374.4 | | |
| | 405.4 | | |
| | 431.4 | 431.4 | X |
| | 476.5 | 476.5 | X |
| | 518.5 | 518.5 | X |
| | 575.6 | 575.6 | X |
| | 632.7 | 632.7 | X |
| | 665.7 | 665.7 | X |
| Total | | | 12 |
| Total non- | | | 0 |

Our second scenario corresponds to a situation commonly found in practice and a major hurdle for many de novo sequencing algorithms. One or two peaks at a time were deleted from the original target spectrum and the resulting information fed to the algorithm. Ten independently started runs were made in every case.

For every group of ten runs, if the correct peptide was found, it was always among the highest scoring sequences reported. Whenever an incorrect sequence was reported as the answer in a GA run, the fitness of the solution was highly correlated with the level of similarity between the answer and the correct sequence. For example, when the 114.16 entry was deleted from the original spectrum, the following ten answers were reported by the GA:

TABLE 8

Results from Sample Run of Method on Incomplete Data

| Sequence | | Fitness |
|---|---|---|
| SEQ ID NO: 2 | L F S Q V G K | 21.5455 |
| SEQ ID NO: 2 | L F S Q V G K | 21.5455 |
| SEQ ID NO: 2 | L F S Q V G K | 21.5455 |
| SEQ ID NO: 2 | L F S Q V G K | 21.5455 |
| SEQ ID NO: 32 | L F S A G V G K | 21.4805 |
| SEQ ID NO: 32 | L F S A G V G K | 21.4805 |
| SEQ ID NO: 33 | L F G T G V G K | 16.1818 |
| SEQ ID NO: 34 | L M C Q V G K | 14.5152 |
| SEQ ID NO: 35 | T F V Q V G K | 13.5758 |
| SEQ ID NO: 36 | L F S Q G S Q R K | 11.7537 |

Each of the reported answers is the result of 150 generations, starting every time with a randomly generated population of amino acid sequences.

As we have pointed out before for the second highest scoring-sequence, LFSAGYGK, the residues A and G have a combined mass equal to that of the Q amino acid residue. Despite the fact that this sequence matches the molecular weight of the target peptide exactly, our implementation has recognized a greater similarity between the correct sequence and the target spectrum and rewarded the answer accordingly. This behavior, where peptides that are very similar to the one that produced the experimental spectrum have very high fitness but not as high as the correct answer, is exactly what we were trying to achieve with our algorithm. Results of runs where a different peak was missing from the target spectrum yielded very similar answers. The correct solution was found among the ten runs every time when only one peak in the target spectrum was missing and it was, in all cases, the highest or second highest-scoring sequence.

Whenever two different peaks were deleted in the target spectrum, the number of times the correct sequence was found was, in general, smaller than when only one peak was missing. Still, the correct peptide was found in many cases. Some examples of the answers found follow. Where peaks at 114.16 and 204.23 were missing:

TABLE 9

| Results from Sample Run of Method on Incomplete Data | | |
|---|---|---|
| Sequence | | Fitness |
| SEQ ID NO: 2 | L F S Q V G K | 19.6667 |
| SEQ ID NO: 2 | L F S Q V G K | 19.6667 |
| SEQ ID NO: 2 | L F S Q V G K | 19.6667 |
| SEQ ID NO: 2 | L F S Q V G K | 19.6667 |
| SEQ ID NO: 31 | L F S G A V G K | 19.5714 |
| SEQ ID NO: 37 | L H P Q V G K | 12.8333 |
| SEQ ID NO: 38 | L F S Q R S R Q R K | 11.7797 |
| SEQ ID NO: 39 | L F S Q R Q R K | 11.7178 |
| SEQ ID NO: 39 | L F S Q R Q R K | 11.7178 |
| SEQ ID NO: 35 | T F V Q V G K | 11.6667 |

The peaks missing correspond to a b-ion for L (114.16) and a y-ion for V (147.18). The correct peptide was found because the remaining peaks still possess enough information to deduct the presence of Leucine and Valine in the sequence in the form of one y-ion and one b-ion for each amino acid respectively. Even though it is true that deleting peaks in this way leaves, in theory, evidence of the presence of every amino acid in the target peptide, the GA does not need prior assignment of spectral data to a particular type of ion or complete ion sequences to find the correct solution and this sets it apart from other de novo reconstructing techniques.

When the peaks missing were 575.68 and 632.73, the answers found were:

TABLE 10

| Results from Sample Run of Method on Incomplete Data | | |
|---|---|---|
| Sequence | | Fitness |
| SEQ ID NO: 2 | L F S Q V G K | 19.8333 |
| SEQ ID NO: 2 | L F S Q V G K | 19.8333 |
| SEQ ID NO: 2 | L F S Q V G K | 19.8333 |
| SEQ ID NO: 2 | L F S Q V G K | 19.8333 |
| SEQ ID NO: 32 | L F S A G V G K | 19.5714 |
| SEO ID NO: 31 | L F S G A V G K | 19.5714 |
| SEQ ID NO: 40 | L F S Q F S Q V G K | 19.1139 |
| SEQ ID NO: 40 | L F S Q F S Q V G K | 19.1139 |

TABLE 10-continued

| Results from Sample Run of Method on Incomplete Data | | |
|---|---|---|
| Sequence | | Fitness |
| SEQ ID NO: 41 | L C M G A V G K | 13 |
| SEQ ID NO: 42 | L F S Q F W A G G K | 14.5583 |

An instance where the correct answer could not be found after ten runs of the GA occurred when the 348.42 and 431.49 peaks were eliminated. Elimination of these contiguous peaks produces a relatively wide spectral region with no information and the GA is forced to guess at the contents of the empty space. The solutions found in this case were:

TABLE 11

| Results from Sample Run of Method on Incomplete Data | | |
|---|---|---|
| Sequence | | Fitness |
| SEQ ID NO: 33 | L F G T G V G K | 21.2857 |
| SEQ ID NO: 33 | L F G T G V G K | 21.2857 |
| SEQ ID NO: 43 | L F T G G V G K | 21.2857 |
| SEQ ID NO: 43 | L F T G G V G K | 21.2857 |
| SEQ ID NO: 43 | L F T G G V G K | 21.2857 |
| SEQ ID NO: 43 | L F T G G V G K | 21.2857 |
| SEQ ID NO: 33 | L F G T G V G K | 21.2857 |
| SEQ ID NO: 43 | L F T G G V G K | 21.2857 |
| SEQ ID NO: 44 | L F R T G G K | 17.1568 |
| SEQ ID NO: 44 | L F R T G G K | 17.1568 |

Notice that incorrect amino acids are inserted in the section of the peptide for which no spectral information is available. The top-scoring sequences reported match the full peptide weight and the m/z information provided. It should be clear that, as the lack of information increases, the GA will produce only partially correct answers with more frequency. For the sake of completeness, we evaluated the fitness of the correct sequence using the same target spectrum (348.42 and 431.49 peaks were eliminated) as the one employed for the ten answers just shown. The fitness of the correct chain is 19.6667. Once again, this is an indication that missing or misleading information can make our algorithm find relatively good solutions that score higher than the sequence we are looking for. This fact also signals the need to develop threshold criteria for the fitness of solutions reported by this or other de novo sequencing algorithms that are based on sound theoretical or empirical probability measures.

TABLE 12

| Results from Sample Run of Method on Incomplete Data | | | | | | | | | | | | |
|---|---|---|---|---|---|---|---|---|---|---|---|---|
| | Peak missing | | | | | | | | | | | |
| Peak missing | 114.16 | 147.18 | 204.23 | 261.34 | 303.36 | 348.42 | 431.49 | 476.55 | 518.57 | 575.68 | 632.73 | 665.75 |
| 114.16 | 4 | 4 | 0 | 1 | 0 | 1 | 0 | 0 | 2 | 2 | 4 | 1 |
| 147.18 | | 5 | 3 | 7 | 3 | 4 | 3 | 2 | 5 | 3 | 0 | 4 |
| 204.23 | | | 1 | 3 | 4 | 3 | 4 | 2 | 2 | 0 | 5 | 4 |

TABLE 12-continued

Results from Sample Run of Method on Incomplete Data

| | Peak missing | | | | | | | | | | | |
|---|---|---|---|---|---|---|---|---|---|---|---|---|
| Peak missing | 114.16 | 147.18 | 204.23 | 261.34 | 303.36 | 348.42 | 431.49 | 476.55 | 518.57 | 575.68 | 632.73 | 665.75 |
| 261.34 | | | | 3 | 3 | 3 | 1 | 3 | 0 | 5 | 6 | 3 |
| 303.36 | | | | | 2 | 0 | 2 | 0 | 2 | 2 | 3 | 2 |
| 348.42 | | | | | | 4 | 0 | 0 | 5 | 0 | 3 | 0 |
| 431.49 | | | | | | | 3 | 4 | 6 | 4 | 4 | 2 |
| 476.55 | | | | | | | | 2 | 1 | 3 | 1 | 2 |
| 518.57 | | | | | | | | | 4 | 7 | 7 | 2 |
| 575.68 | | | | | | | | | | 1 | 7 | 1 |
| 632.73 | | | | | | | | | | | 4 | 5 |
| 665.75 | | | | | | | | | | | | 3 |

A summary of the number of times that the correct sequence was found in every set of ten runs when one and two peaks in the target spectrum were missing, is shown in Table 12. The numbers shown in this table are a crude simplification of the answers provided by the algorithm since counting only the number of perfect solutions dismisses the fact that all the peptides reported as answers could be partially matched to relatively large portions of the available data. The peptides obtained in these runs are structurally very similar to the ones we have already shown for the cases of one and two-missing target peaks.

As with other heuristic optimization methodologies, the GA will sometimes produce different answers in different runs and multiple starts may be necessary to find a satisfactory solution. The fact that distinct solutions may be produced using the same target data after multiple runs must be seen more as an asset than a problem. Since actual MS/MS spectra are likely to have missing, misleading and noisy information, any effective de novo algorithm must provide a way of dealing with these characteristics and, in the end, the user will be forced to examine a series of sequences that seem to fit the available data well.

The version of the GA discussed herein is not automatically deterred by missing or incorrect information although, naturally, the quality of the solution obtained will depend on how representative the input data is of the actual sequence.

Computational Efficiency

As we have implemented it, our version of the GA goes through 350*150=52,500 evaluations of the objective function before reporting an answer. Considering that we have used at least ten independently started runs to find a series of potential sequences from which we can select a final peptide, our algorithm goes through at most 525,000 distinct sequences to build a small set of potentially good amino acid chains.

For the example we have presented here, we considered solutions with up to 10 amino acids each. Our set of building blocks consists of 19 different amino acids (we cannot distinguish between Leu and Ile) and a blank character. The number of distinct candidate peptide chains available under these conditions equals $20^{10} \approx 1.024 \times 10^{13}$. This means that our algorithm has explored at most $5.13 \times 10^{-6}$% of the available space before reporting an answer.

We cannot reasonably expect that the population sizes and other GA parameters used in this paper will be equally effective for problems of all sizes, against very noisy data or in cases with severely incomplete spectra. In general, larger population sizes will result in a more thorough exploration of the feasible space but, given the number of possible peptide sequences for any problem of practical importance, it is clear that we should concentrate our efforts developing solution methodologies that, like the GA, search the available space in more efficient ways. Potentially, very large populations could be needed as the length of the amino acid chains considered increases.

Fortunately, the user has the ability of determining, prior to an actual run, the computational effort required of the GA to obtain an answer by choosing convergence criteria and population sizes. The GA has proved to remain practically useful for problems that grow exponentially with the number of decision variables in areas of reliability engineering and experimental design. This means that the algorithm has been shown to be capable of finding good answers in problems with very large spaces without using an exponentially increasing population size.

Even with further developments on effective and efficient algorithm for de novo sequencing, many of the features of actual MS/MS spectra that make the problem difficult to solve will remain. In the absence of a reliable method to identify peaks produced by specific ion types, there will always be a chance that peaks from a variety of ion types match, erroneously, the mass of an amino acid residue. When this happens, our algorithm may assign the matching residue to that position in the peptide and converge to the wrong final chain. As the length of the target peptide increases, so will the chances of this type of erroneous matching, particularly if the level of noise in the target spectrum is considerable. This problem underscores the importance of incorporating as much information as possible into the solution algorithm regarding the identity of target spectral features.

Remarks Regarding Application of Genetic Algorithm to Peptide Identification

Several modifications to the method presented here are possible, though remaining within the scope of the present invention. For instance, coupling the procedures developed for our GA with a probability-based evaluation function such as that described above will allow us to score peptides on a likelihood scale. Agreeing on a scoring function is vital if a performance comparison with other de novo techniques, or other peptide identification algorithms, is to take place. In addition, the spectra created by the GA for every potential solution in this discussion consisted of b- and y-ion types only. It is possible that simulation of other ion types could make identification easier when dealing with actual MS/MS spectra.

Furthermore, the examples presented in the discussion of this GA application have used highly idealized spectra. Use of experimental MS/MS spectra will almost certainly involve less accurate data and this will make the GA produce a number of sequences that match the available information equally well (or equally poorly). In those cases, the algorithm presented here might be supplemented with information gathered from other sources and one's good judgment, as is within the ability of one skilled in the art. In this regard, the creation of a hybrid de novo algorithm that uses a combination of graph-theoretical and GA procedures to build amino acid sequences would be beneficial, for example. The joint use of GA and other optimization algorithms has proved very successful in other areas of combinatorial optimization. For the reconstruction of peptides from MS/MS data, the inclusion of sequences created using a directed graph with spectral information can greatly reduce the computational effort needed by concentrating the resources of the GA to a neighborhood of highly likely peptides. This can be particularly useful once the size of the target peptide exceeds a certain threshold.

Further development of a fitness function that allows the optimal sequence to be approached in a more gradual way may be needed when dealing with real spectra. As we have pointed out, one of the main problems with peptide sequencing using MS/MS data is that two very similar amino acid chains would produce MS/MS spectra that are seemingly very different. We have developed an initial approach to solve this problem that allows us to detect similarities by matching fractions of two different spectra, though variations on this technique may be applied without undue experimentation, and may give better results.

We have stated the problem of reconstructing a peptide starting with MS/MS data as the optimization of a fitness function and then solved a simple example using genetic algorithms. Unlike other de novo construction techniques, this exemplary methodology starts with complete sequences and attempts gradually to find one that matches the target spectrum optimally.

The GA presented above is not immediately deterred by incomplete spectra, peaks produced by unusually occurring peptide fragments or background noise. On the other hand, starting with a population of peptides generated at random forces the algorithm to explore regions of the problem space that are probably nowhere close to the correct answer.

The growth in computational effort needed to run the GA can be controlled by the user, preventing the exponential explosion in resource utilization that occurs with other de novo techniques. Although in theory a very small population could be used, practical applications suggest that relatively large initial populations (perhaps in the order of a few thousands) may be necessary for very complex problem environments.

All publications and other documents cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that would occur to one skilled in the relevant art are desired to be protected.

We claim:

1. A method of finding one or more possible matching peptides to a test peptide associated with a tandem mass spectrometry test spectrum, comprising:

with a computer, selecting an objective function $f$ that includes at least one term comprising the number of peaks, $\eta$, that appear in both a test spectrum, $s_1$ and a simulated spectrum of one of a plurality of candidate peptide, $s_2$, wherein $\eta$ indicates the number of peaks in $s_1$ with corresponding peaks in $s_2$ and the number of peaks in $s_1$ that are translated in $s_2$ ; and performing a genetic algorithm on a plurality of candidate peptides using the obejective function $f$, wherein the act of performing comprises determining and storing $\eta$ for $s_1$ and $s_2$.

2. The method of claim 1, wherein the plurality of candidate peptides is a first set of candidate peptides, and wherein the method further comprises:

using $\eta$ to select the one of the plurality of candidate peptides as a possible matching peptide for the test peptide associated with the tandem mass spectrometry test spectrum; and generating a second set of candidate peptides, the second set of candidate peptides including the one of the plurality of candidate peptides and one or more modified versions of the one of the plurality of candidate peptides.

3. The method of claim 1, wherein the act of determining $\eta$ for $s_1$ and $s_2$ comprises:

creating an $m_1 \times m_2$ matrix, M, where:

$m_1$ is the number of peaks in $s_1$;

$m_2$ is the number of peaks in $s_2$; and the cell of M at row i, column j, holds a number representative of the signed difference between the location of peak i in $s_1$ and peak j in $s_2$; and assigning $\eta$ to be the number of non-distinct values in M.

4. The method of claim 1, wherein the act of determining $\eta$ for $s_1$ and $s_2$ comprises:

creating an $m_1 \times m_2$ matrix, M, where:

$m_1$ is the number of peaks in $s_1$;

$m_2$ is the number of peaks in $s_2$; and the cell of M at row i, column j, holds a number representative of the signed difference between the location of peak i in $s_1$ and peak j in $s_2$; and assigning $\eta$ to be the maximum number of times a non-distinct value appears in M.

5. The method of claim 1, where the function $f$ includes additional terms, the additional terms comprising a value that indicates the number of matching peaks between the spectra $s_1$ and $s_2$, a value that indicates the number of nonmatching peaks between the spectra $s_1$ and $s_2$, and a value that indicates the deviation between the mass of a respective candidate peptide and the test peptide.

6. The method of claim 1, wherein the act of performing further comprises:

computing fitness values for the plurality of candidate peptides using the objective function $f$; and selecting one or more of the candidate peptides as possible matching peptides based on the computed fitness values.

7. The method of claim 6, wherein the plurality of candidate peptides is a first set of candidate peptides, and wherein the act of performing further comprises:

altering at least some of the selected candidate peptides; and creating a second set of candidate peptides, the second set of candidate peptides comprising the selected candidate peptides and the altered candidate peptides.

8. The method of claim 7, further comprising repeating the acts of computing and selecting for the candidate peptides in the second set of candidate peptides.

9. A method of identifying an unknown peptide, comprising:

with a computer, generating a simulated tandem-mass spectrometry spectrum for a candidate peptide;

determining mass-to-charge ratio differences between spectral peaks of the simulated spectrum and corresponding spectral peaks of an observed spectrum produced by an unknown peptide;

determining the number of non-distinct mass-to-charge ratio differences that exist among the mass-to-charge ratio differences; and measuring similarities between the simulated spectrum and the observed spectrum produced by the unknown peptide using an objective function that includes as one of multiple terms the number of non-distinct mass-to-charge ratio differences.

10. The method of claim 9, wherein the act of determining the number of non-distinct mass-to-charge ratio differences comprises determining a value indicating how many of the mass-to-charge ratio differences differ from each other by less than a given tolerance.

11. The method of claim 9, further comprising eliminating the candidate peptide as a possible match for the unknown peptide based in part on the determined mass-to-charge ratio differences.

12. The method of claim 9, wherein the act of generating a simulated tandem-mass spectrometry spectrum for a candidate peptide comprises breaking the candidate peptide into charged peptide fragments.

13. A method of identifying an unknown amino acid sequence, comprising:
with a computer,
generating a first set of candidate amino acid sequences;
producing simulated spectra for respective amino acid sequences of the first set;
evaluating the simulated spectra relative to an observed spectrum produced by the unknown amino acid sequence by computing fitness values representative of how similar the observed spectrum is to respective ones of the simulated spectra, the fitness values being computed by an objective function, the objective function including a term indicative of the number of non-distinct peaks between the simulated spectra and the observed spectrum;
selecting one or more candidate amino acid sequences from the first set based on the fitness values;
modifying one or more of the selected amino acid sequences; and
generating a second set of candidate amino acid sequences, the second set comprising the selected amino acid sequences and the modified amino acid sequences.

14. The method of claim 13, repeating the acts of producing, evaluating, and selecting using the second set as the first set.

15. The method of claim 13, wherein the act of modifying comprises randomly replacing amino acids in the one or more of the selected candidate amino acid sequences, inserting new amino acids into the one or more of the selected candidate amino acid sequences, or inverting one or more amino acids in the one or more of the selected candidate amino acid sequences.

16. The method of claim 13, wherein the act of generating the first set comprises randomly generating amino acid sequences.

17. The method of claim 16, wherein the act of generating the first set further comprises:
selecting a first and a second of the randomly generated amino acid sequences;
breaking each of the first and the second randomly generated amino acid sequences into respective first and second portions at randomly selected breaking points; and
generating additional candidate amino acid sequences for the first set by combining the first portion of the first randomly generated amino acid sequence with the second portion of the second randomly generated amino acid sequence and by combining the second portion of the first randomly generated amino acid sequence with the first portion of the second randomly generated amino acid sequence.

18. The method of claim 13, wherein the term is determined by generating and storing an $m_1 \times m_2$ matrix M, where:
$m_1$ is the number of peaks in a respective one of the simulated spectra,
$m_2$ is the number of peaks in the observed spectrum, and
the cells of M are numbers representative of the signed difference between the location of a spectral peak in the respective one of the simulated spectra and a corresponding spectral peak in the observed spectrum, and wherein the term is the number of times a non-distinct value appears in the matrix M.

* * * * *

SEQUENCE LISTING

```
<160> NUMBER OF SEQ ID NOS: 44

<210> SEQ ID NO 1
<211> LENGTH: 14
<212> TYPE: PRT
<213> ORGANISM: Deinococcus radiodurans

<400> SEQUENCE: 1

Pro Gly Ile Asp Phe Thr Asn Asp Pro Leu Leu Gln Gly Arg
1               5                   10


<210> SEQ ID NO 2
<211> LENGTH: 7
<212> TYPE: PRT
<213> ORGANISM: Deinococcus radiodurans

<400> SEQUENCE: 2

Leu Phe Ser Gln Val Gly Lys
1               5


<210> SEQ ID NO 3
<211> LENGTH: 7
<212> TYPE: PRT
<213> ORGANISM: artificial sequence
<220> FEATURE:
<223> OTHER INFORMATION: hypothetical sequence generated for purpose of
      describing the invention

<400> SEQUENCE: 3

Val Gln Ser Gly Lys Met Gly
1               5
```

```
<210> SEQ ID NO 4
<211> LENGTH: 9
<212> TYPE: PRT
<213> ORGANISM: artificial sequence
<220> FEATURE:
<223> OTHER INFORMATION: hypothetical sequence generated for purpose of
      describing the invention

<400> SEQUENCE: 4

Phe Ser Gln Asp Met Tyr Val Gln Arg
1               5


<210> SEQ ID NO 5
<211> LENGTH: 9
<212> TYPE: PRT
<213> ORGANISM: artificial sequence
<220> FEATURE:
<223> OTHER INFORMATION: hypothetical sequence generated for purpose of
      describing the invention

<400> SEQUENCE: 5

Asn Glu Trp Ala Asn Asn Ser Gln Arg
1               5


<210> SEQ ID NO 6
<211> LENGTH: 4
<212> TYPE: PRT
<213> ORGANISM: artificial sequence
<220> FEATURE:
<223> OTHER INFORMATION: hypothetical sequence generated for purpose of
      describing the invention

<400> SEQUENCE: 6

Val Gln Ser Arg
1


<210> SEQ ID NO 7
<211> LENGTH: 10
<212> TYPE: PRT
<213> ORGANISM: artificial sequence
<220> FEATURE:
<223> OTHER INFORMATION: hypothetical sequence generated for purpose of
      describing the invention

<400> SEQUENCE: 7

Arg Gln Ser Thr Cys Ala Arg Phe Ser Phe
1               5                   10


<210> SEQ ID NO 8
<211> LENGTH: 10
<212> TYPE: PRT
<213> ORGANISM: artificial sequence
<220> FEATURE:
<223> OTHER INFORMATION: hypothetical sequence generated for purpose of
      describing the invention

<400> SEQUENCE: 8

Thr Asp Ser Cys Thr Val Gln Val Cys Trp
1               5                   10


<210> SEQ ID NO 9
<211> LENGTH: 10
<212> TYPE: PRT
<213> ORGANISM: artificial sequence
<220> FEATURE:
<223> OTHER INFORMATION: hypothetical sequence generated for purpose of
      describing the invention
```

<400> SEQUENCE: 9

Trp Arg Ser Gly Asp Pro Met Leu Gln Phe
1 5 10

<210> SEQ ID NO 10
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 10

Asp Ser Asn Lys Lys Cys Gly Thr Asn Glu
1 5 10

<210> SEQ ID NO 11
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 11

Ala Glu Leu Gln Asn Cys Arg Lys Gln Phe
1 5 10

<210> SEQ ID NO 12
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 12

Cys Met Asn Pro Arg Phe Glu Ser Leu Gln
1 5 10

<210> SEQ ID NO 13
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 13

Phe Trp Ser Thr Asp Ala His Lys Pro Leu
1 5 10

<210> SEQ ID NO 14
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 14

Pro Val Leu Ser Tyr Ser Glu Glu Thr His
1 5 10

<210> SEQ ID NO 15
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 15

Ser Trp Arg Leu Met Trp Gln Lys Lys Phe
1 5 10

<210> SEQ ID NO 16
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 16

Gln Asn Asn Glu Phe Gln Met Cys Asp Val
1 5 10

<210> SEQ ID NO 17
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 17

Asn Cys Gly Phe Gln Asn Ser Met Asp Asp
1 5 10

<210> SEQ ID NO 18
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 18

Cys His Lys Leu Asn Thr Pro Phe Ser His
1 5 10

<210> SEQ ID NO 19
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 19

Phe Phe Cys Val Asp Tyr Thr Pro Arg His
1 5 10

<210> SEQ ID NO 20
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 20

Asn Arg Val Ala Val Asn Phe Cys Thr Pro
1 5 10

<210> SEQ ID NO 21
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 21

Leu Gln His Glu Cys Val Asn Gly Leu Tyr
1 5 10

<210> SEQ ID NO 22
<211> LENGTH: 10
<212> TYPE: PRT
<213> ORGANISM: artificial sequence
<220> FEATURE:
<223> OTHER INFORMATION: hypothetical sequence generated for purpose of describing the invention

<400> SEQUENCE: 22

Phe Tyr Gly Asn Gly Arg Pro Gly Leu Lys
1 5 10

<210> SEQ ID NO 23
<211> LENGTH: 6
<212> TYPE: PRT
<213> ORGANISM: artificial sequence
<220> FEATURE:
<223> OTHER INFORMATION: hypothetical sequence formed by adjoining alternate portions of parent individuals

<400> SEQUENCE: 23

Thr Asp Ser Cys Ser Arg
1 5

<210> SEQ ID NO 24
<211> LENGTH: 6
<212> TYPE: PRT
<213> ORGANISM: artificial sequence
<220> FEATURE:
<223> OTHER INFORMATION: hypothetical sequence including a substitution mutation

<400> SEQUENCE: 24

Thr Asp Ser Lys Met Arg
1 5

<210> SEQ ID NO 25
<211> LENGTH: 9
<212> TYPE: PRT
<213> ORGANISM: artificial sequence
<220> FEATURE:
<223> OTHER INFORMATION: hypothetical sequence including an insertion mutation

<400> SEQUENCE: 25

Thr Gly Asp Ser Cys Val Tyr Ser Arg
1 5

<210> SEQ ID NO 26
<211> LENGTH: 6
<212> TYPE: PRT
<213> ORGANISM: artificial sequence <220>
<220> FEATURE:
<223> OTHER INFORMATION: hypothetical sequence including an inversion mutation

<400> SEQUENCE: 26

Thr Ser Cys Ser Asp Arg
1 5

<210> SEQ ID NO 27
<211> LENGTH: 5
<212> TYPE: PRT
<213> ORGANISM: artificial sequence
<220> FEATURE:
<223> OTHER INFORMATION: hypothetical sequence including a portion of a protein created in a recombination step.

<400> SEQUENCE: 27

Asp Ser Cys Ser Arg
1 5

<210> SEQ ID NO 28
<211> LENGTH: 4
<212> TYPE: PRT
<213> ORGANISM: artificial sequence
<220> FEATURE:
<223> OTHER INFORMATION: hypothetical sequence including a portion of a protein created in a recombination step.

<400> SEQUENCE: 28

Ser Cys Ser Arg
1

<210> SEQ ID NO 29
<211> LENGTH: 7
<212> TYPE: PRT
<213> ORGANISM: artificial sequence <220>
<220> FEATURE:
<223> OTHER INFORMATION: hypothetical sequence generated for purpose of describing the invention

<400> SEQUENCE: 29

Leu Gly Ser Gln Val Gly Lys
1 5

<210> SEQ ID NO 30
<211> LENGTH: 8
<212> TYPE: PRT
<213> ORGANISM: artificial sequence
<220> FEATURE:
<223> OTHER INFORMATION: hypothetical sequence generated for purpose of describing the invention

<400> SEQUENCE: 30

Ala Pro Ala His Val Val Gly Lys
1 5

<210> SEQ ID NO 31
<211> LENGTH: 8
<212> TYPE: PRT
<213> ORGANISM: artificial sequence <220>
<220> FEATURE:
<223> OTHER INFORMATION: hypothetical sequence generated for purpose of describing the invention

<400> SEQUENCE: 31

Leu Phe Ser Gly Ala Val Gly Lys
1 5

<210> SEQ ID NO 32
<211> LENGTH: 8
<212> TYPE: PRT
<213> ORGANISM: artificial sequence
<220> FEATURE:
<223> OTHER INFORMATION: hypothetical sequence deduced in accordance with the invention

<400> SEQUENCE: 32

Leu Phe Ser Ala Gly Val Gly Lys
1 5

<210> SEQ ID NO 33
<211> LENGTH: 8
<212> TYPE: PRT
<213> ORGANISM: artificial sequence
<220> FEATURE:
<223> OTHER INFORMATION: hypothetical sequence deduced in accordance with the invention

<400> SEQUENCE: 33

Leu Phe Gly Thr Gly Val Gly Lys
1 5

<210> SEQ ID NO 34
<211> LENGTH: 7
<212> TYPE: PRT
<213> ORGANISM: artificial sequence
<220> FEATURE:
<223> OTHER INFORMATION: hypothetical sequence deduced in accordance with the invention

<400> SEQUENCE: 34

Leu Met Cys Gln Val Gly Lys
1 5

<210> SEQ ID NO 35
<211> LENGTH: 7
<212> TYPE: PRT
<213> ORGANISM: artificial sequence
<220> FEATURE:
<223> OTHER INFORMATION: hypothetical sequence deduced in accordance with the invention

<400> SEQUENCE: 35

Thr Phe Val Gln Val Gly Lys
1 5

<210> SEQ ID NO 36
<211> LENGTH: 9
<212> TYPE: PRT
<213> ORGANISM: artificial sequence
<220> FEATURE:
<223> OTHER INFORMATION: hypothetical sequence deduced in accordance with the invention

<400> SEQUENCE: 36

Leu Phe Ser Gln Gly Ser Gln Arg Lys
1 5

<210> SEQ ID NO 37
<211> LENGTH: 7
<212> TYPE: PRT
<213> ORGANISM: artificial sequence
<220> FEATURE:
<223> OTHER INFORMATION: hypothetical sequence deduced in accordance with the invention

<400> SEQUENCE: 37

Leu His Pro Gln Val Gly Lys
1 5

<210> SEQ ID NO 38
<211> LENGTH: 10
<212> TYPE: PRT
<213> ORGANISM: artificial sequence
<220> FEATURE:
<223> OTHER INFORMATION: hypothetical sequence deduced in accordance with the invention

<400> SEQUENCE: 38

```
Leu Phe Ser Gln Arg Ser Arg Gln Arg Lys
1               5                   10
```

<210> SEQ ID NO 39
<211> LENGTH: 8
<212> TYPE: PRT
<213> ORGANISM: artificial sequence
<220> FEATURE:
<223> OTHER INFORMATION: hypothetical sequence deduced in accordance with the invention

<400> SEQUENCE: 39

```
Leu Phe Ser Gln Arg Gln Arg Lys
1               5
```

<210> SEQ ID NO 40
<211> LENGTH: 10
<212> TYPE: PRT
<213> ORGANISM: artificial sequence
<220> FEATURE:
<223> OTHER INFORMATION: hypothetical sequence deduced in accordance with the invention

<400> SEQUENCE: 40

```
Leu Phe Ser Gln Phe Ser Gln Val Gly Lys
1               5                   10
```

<210> SEQ ID NO 41
<211> LENGTH: 8
<212> TYPE: PRT
<213> ORGANISM: artificial sequence
<220> FEATURE:
<223> OTHER INFORMATION: hypothetical sequence deduced in accordance with the invention

<400> SEQUENCE: 41

```
Leu Cys Met Gly Ala Val Gly Lys
1               5
```

<210> SEQ ID NO 42
<211> LENGTH: 10
<212> TYPE: PRT
<213> ORGANISM: artificial sequence
<220> FEATURE:
<223> OTHER INFORMATION: hypothetical sequence deduced in accordance with the invention

<400> SEQUENCE: 42

```
Leu Phe Ser Gln Phe Trp Ala Gly Gly Lys
1               5                   10
```

<210> SEQ ID NO 43
<211> LENGTH: 8
<212> TYPE: PRT
<213> ORGANISM: artificial sequence
<220> FEATURE:
<223> OTHER INFORMATION: hypothetical sequence deduced in accordance with the invention -continued

```
<400> SEQUENCE: 43

Leu Phe Thr Gly Gly Val Gly Lys
1               5


<210> SEQ ID NO 44
<211> LENGTH: 7
<212> TYPE: PRT
<213> ORGANISM: artificial sequence
<220> FEATURE:
<223> OTHER INFORMATION: hypothetical sequence deduced in accordance
      with the invention

<400> SEQUENCE: 44

Leu Phe Arg Thr Gly Gly Lys
1               5
```